United States Patent
Miyata et al.

(10) Patent No.: US 7,820,396 B2
(45) Date of Patent: Oct. 26, 2010

(54) METHOD FOR DETERMINING ATOPIC DERMATITIS USING PROTEIN MARKER

(75) Inventors: Satoshi Miyata, Yokohama (JP); Kaoru Miyazaki, Yokohama (JP); Chie Yasuda, Machida (JP); Akihiro Iwamatsu, Yokohama (JP); Zenro Ikezawa, Yokohama (JP); Michiko Aihara, 3-9-1, Fukuura, Kanazawa-ku, Yokohama-shi, Kanagawa (JP) 236-0004; Kayano Moriyama, 641-12, Maioka-cho, totsuka-ku, Yokohama-shi, Kanagawa (JP) 244-0813

(73) Assignees: Fancl Corporation, Kanagawa (JP); Kaoru Miyazki, Kanagawa (JP); Zentro Ikezawa, Kanagawa (JP); Michiko Aihara, Kanagawa (JP); Kayano Moriyama, Kanagawa (JP)

( * ) Notice: Subject to any disclaimer, the term of this patent is extended or adjusted under 35 U.S.C. 154(b) by 121 days.

(21) Appl. No.: 12/090,644

(22) PCT Filed: Oct. 19, 2006

(86) PCT No.: PCT/JP2006/320836

§ 371 (c)(1),
(2), (4) Date: Apr. 17, 2008

(87) PCT Pub. No.: WO2007/046463

PCT Pub. Date: Apr. 26, 2007

(65) Prior Publication Data

US 2009/0263792 A1 Oct. 22, 2009

(30) Foreign Application Priority Data

Oct. 21, 2005 (JP) .............................. 2005-306498

(51) Int. Cl.
*G01N 33/53* (2006.01)
*G01N 33/567* (2006.01)
(52) U.S. Cl. ....................................... 435/7.1; 436/501
(58) Field of Classification Search ....................... None
See application file for complete search history.

(56) References Cited

FOREIGN PATENT DOCUMENTS

| JP | 2005-110602 | 4/2005 |
| WO | WO 01/65259 A1 | 9/2001 |

OTHER PUBLICATIONS

Bowcock (Human Molecular Genetics (2001) vol. 10, p. 1793).*
K. Mitsuishi, et al, "The squamous cell carcinoma antigens as relevant biomerkers of atopic dermatitis," Clin Exp Allergy 2005, 35, pp. 1327-1333.
M. Toyoda, et al., "Clinical and Laboratory Investigations Nerve Growth factor and substance P are useful plasma markers of disease activity in atopic dermatitis," British Journal of Dermatology 2002, 147, pp. 71-79.
I. Angelova-Fischer, et al., "Significance of interleukin-16, macrophage-derived chemokine, eosinophil cationic protein and soluble E-selectin in reflecting disease activity of atopic dermatitis—from laboratory parameters to clinical scores," British Journal of Dermatology 2006, 154, pp. 1112-1117.
Yong-Doo Park, et al., "Towards a proteomic analysis of atopic dermatitis: A two-dimensional-polyacrylamide gel electrophoresis/mass spectrometric analysis of cultured patient-derived fibroblasts," Proteomics 2004, 4, pp. 3446-3455.
Yong-Doo Park, et al., "Two-dimensional electrophoretic profiling of atopic dermatitis in primary cultured keratinocytes from patients," Protemics 2006, 6, pp. 1362-1370.
Satoshi Miyata, "Finding Proteins Relating to Prevention of Skin Aging," New Material Exploration Group, Central Research Laboratory, Fancl Corporation, pp. 41- 45.
Momoko Takakura, et al., "Differences in Cytokine Production between NC/Nga Mice with and without Atopic-Dermatitis-like Lesion," Nitikawa Kaishi, 2004, vol. 114, No. 2, pp. 1881-1887.

* cited by examiner

*Primary Examiner*—Christine J Saoud
(74) *Attorney, Agent, or Firm*—Knobbe Martens Olson & Bear LLP

(57) ABSTRACT

It is an object of the present invention to find substances that can be used as disease markers for atopic dermatitis and the present invention provides a method for determining atopic dermatitis, including measurement of the expression of specific proteins and/or their genes in skin cells and/or skin tissues, wherein the specific proteins change their expression with inflammation caused by atopic dermatitis or change their expression according to the degree of predisposition to atopic dermatitis. The present invention also provides a kit for determining the degree of inflammation of atopic dermatitis or risk of developing atopic dermatitis, as well as a method for determining substances effective in the treatment and/or prevention of atopic dermatitis.

4 Claims, 15 Drawing Sheets

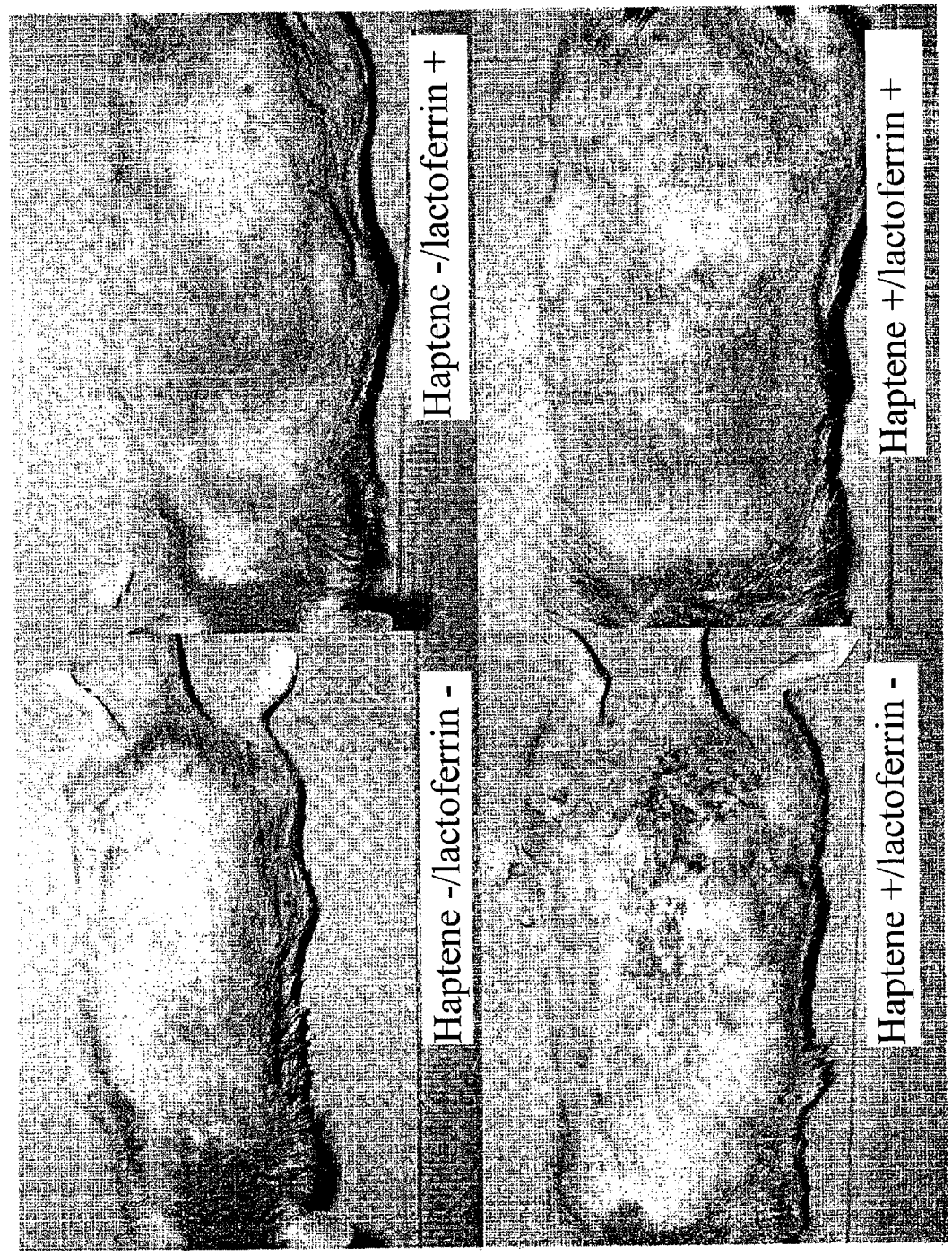
[Fig 1]

[Fig 2(a)]
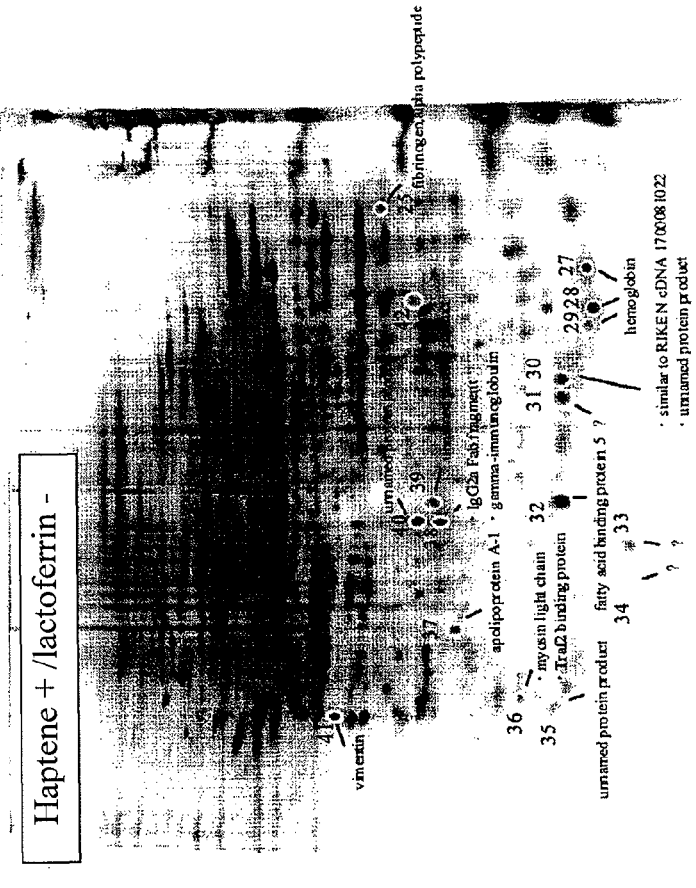
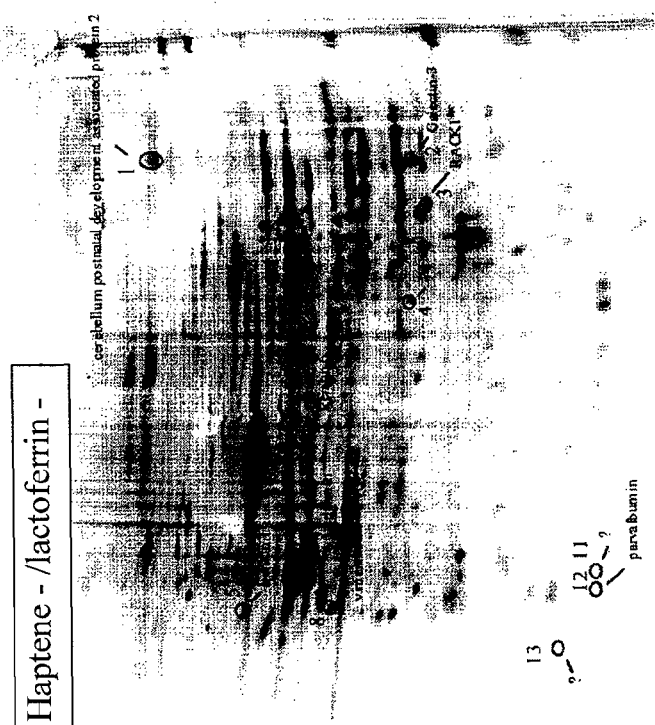
◯ : Protein expressed without haptene treatment
◉ : Protein expressed with haptene treatment

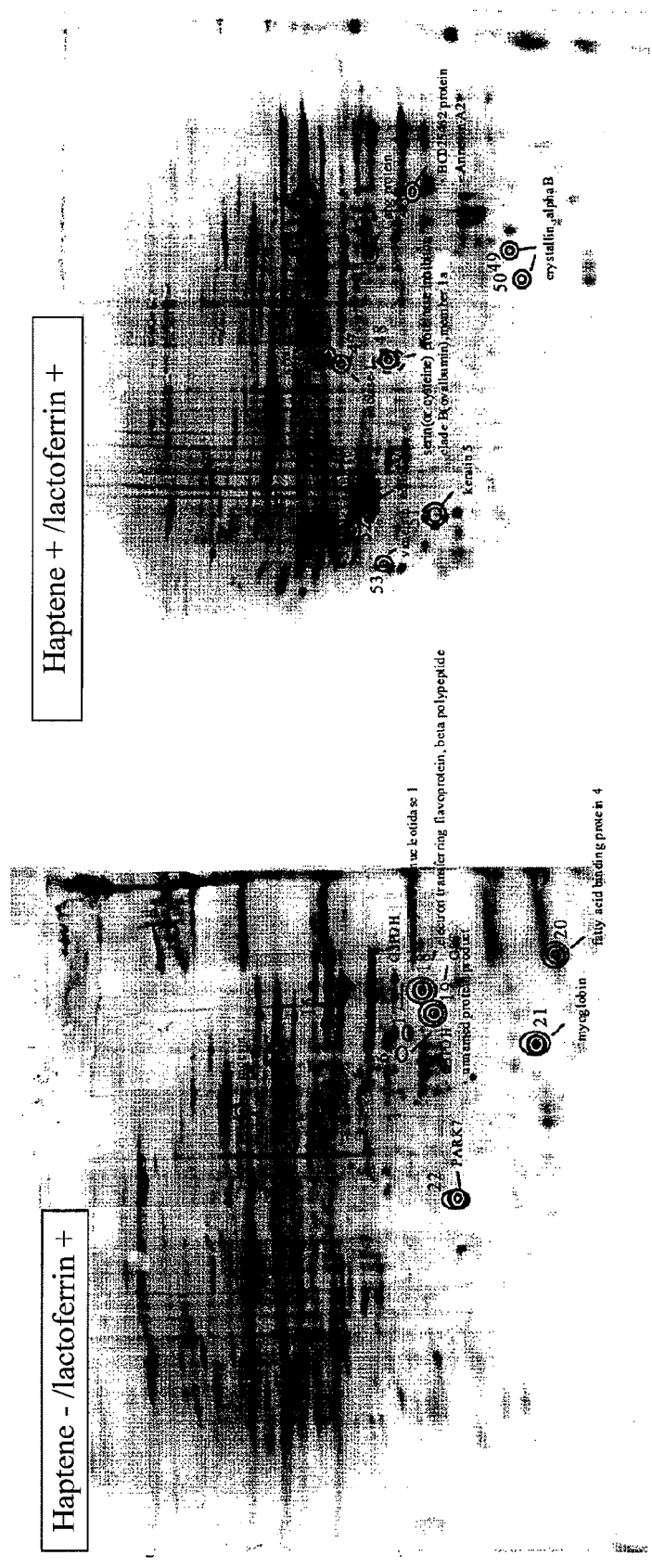
[Fig 2(b)]

[Fig 3]
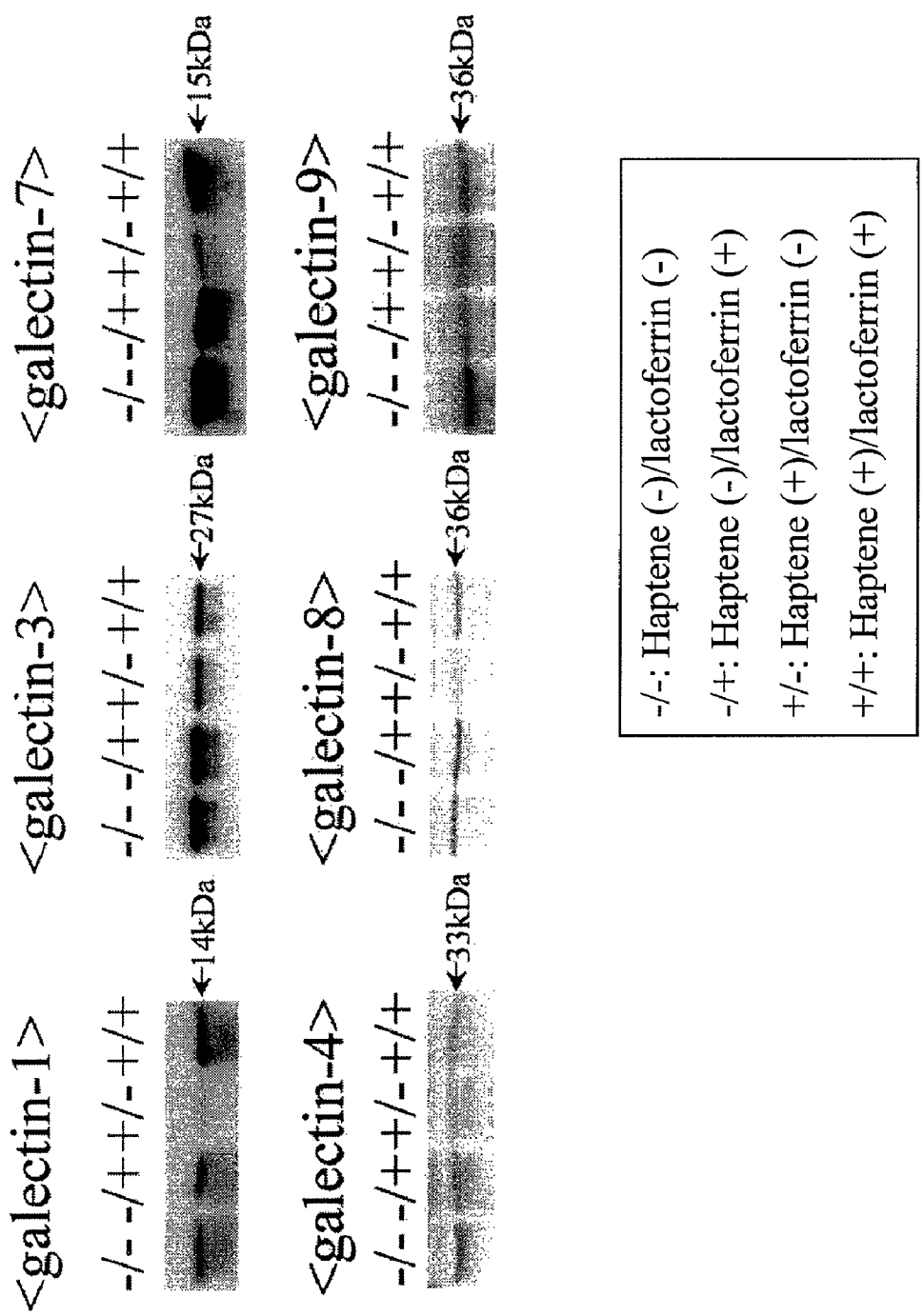

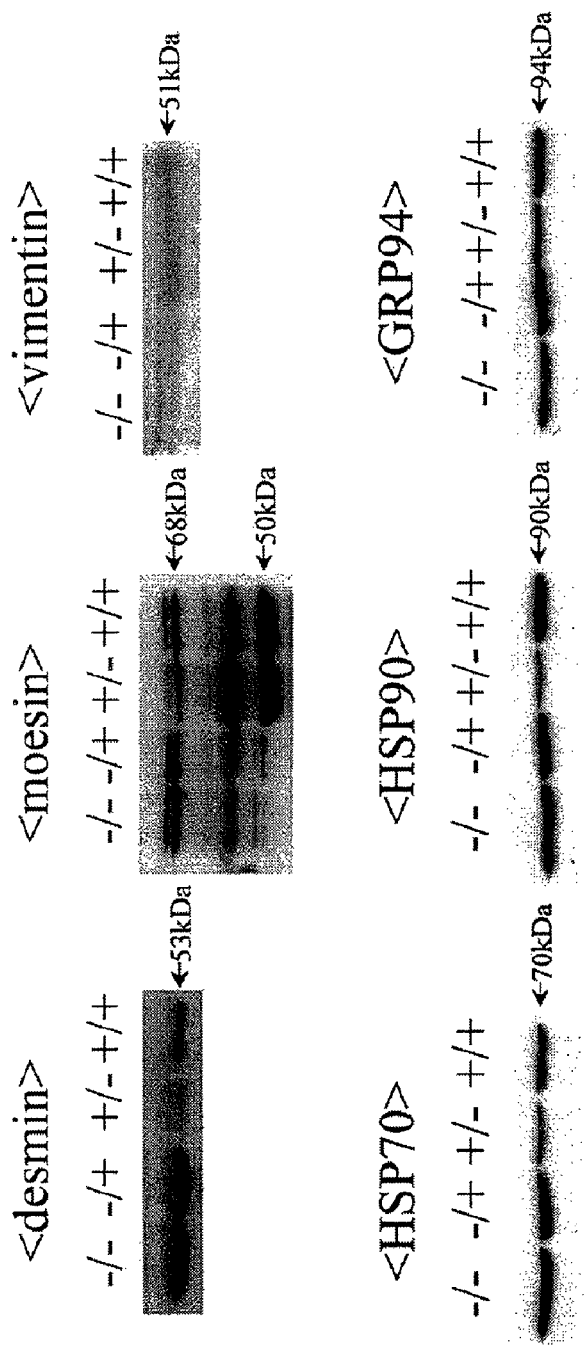
[Fig 4]

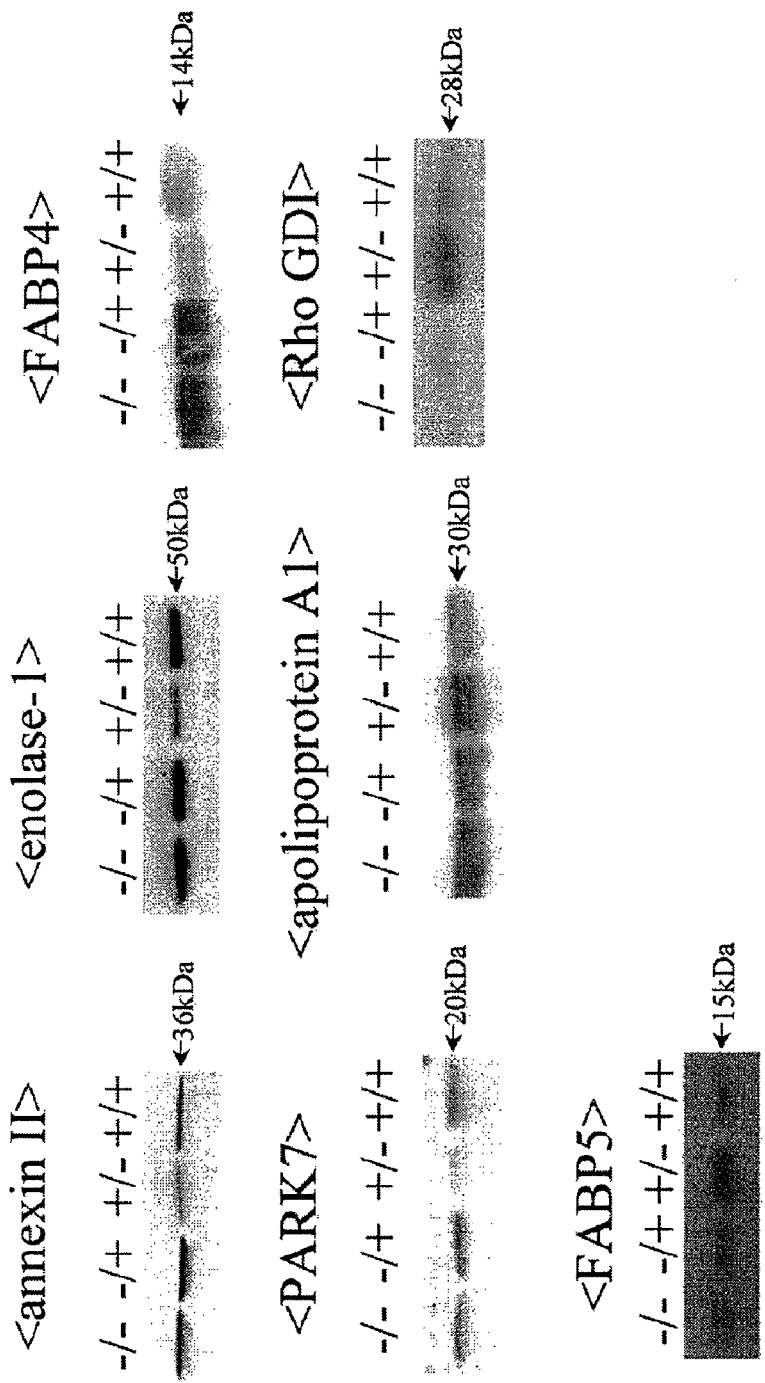
[Fig 5]

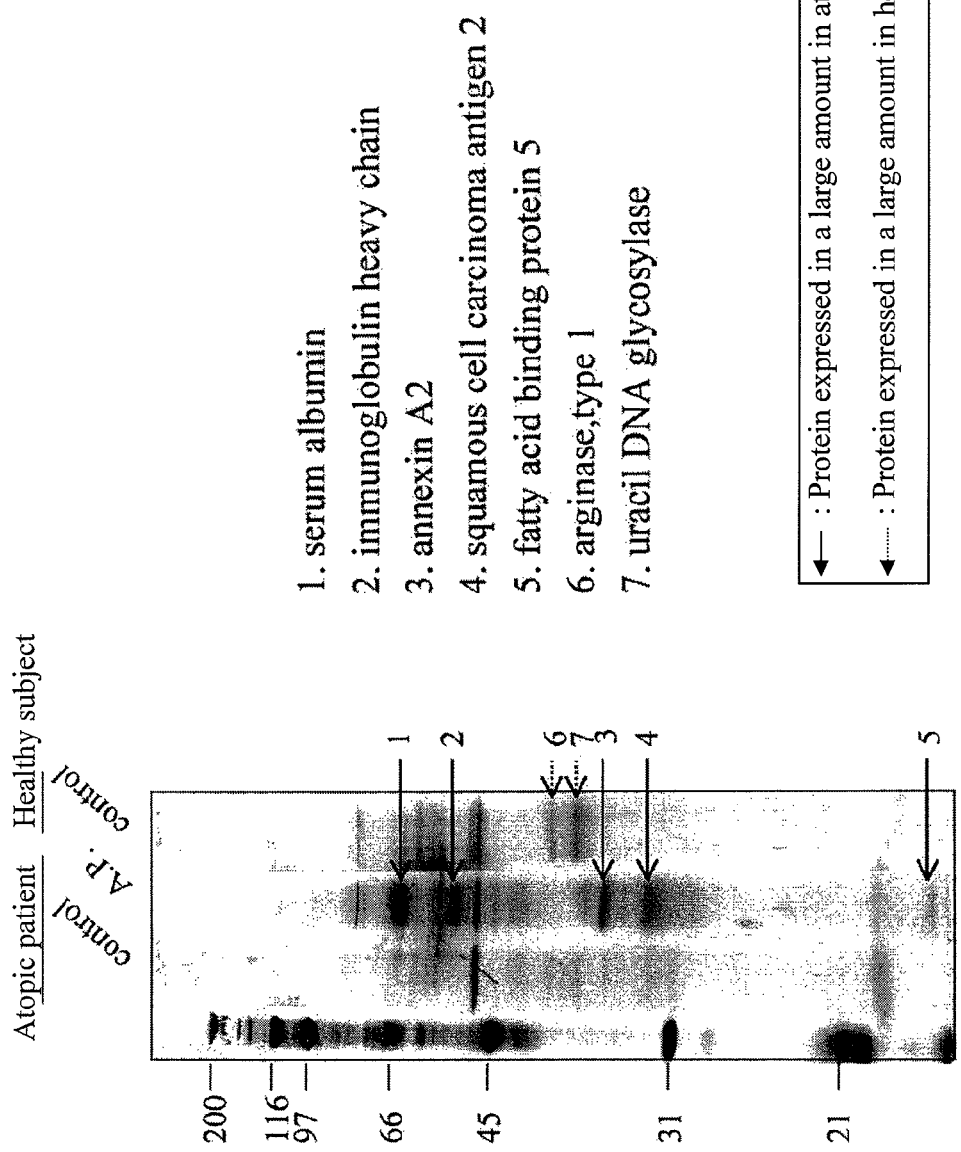

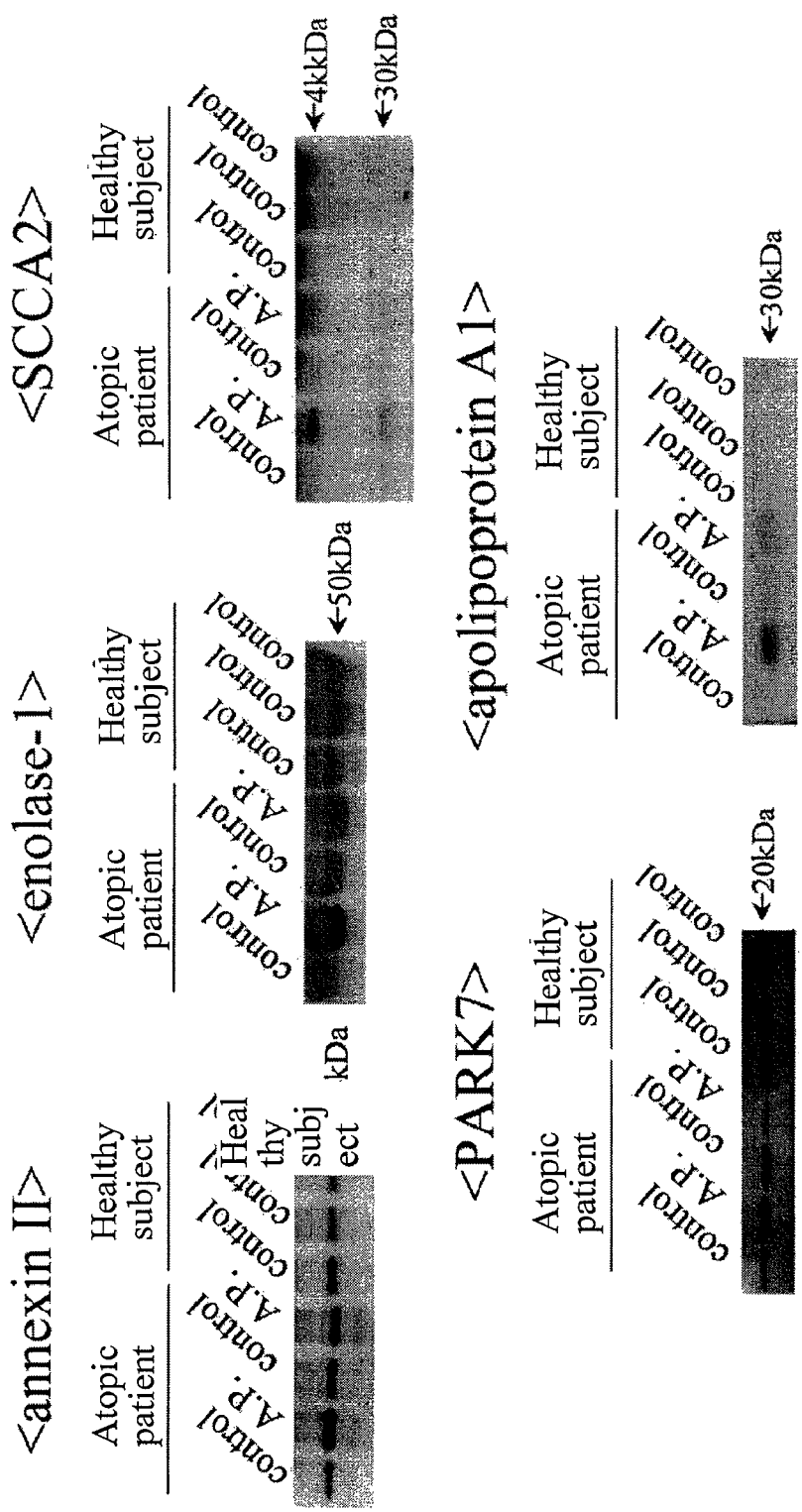
[Fig 7]

[Fig 8(a)]
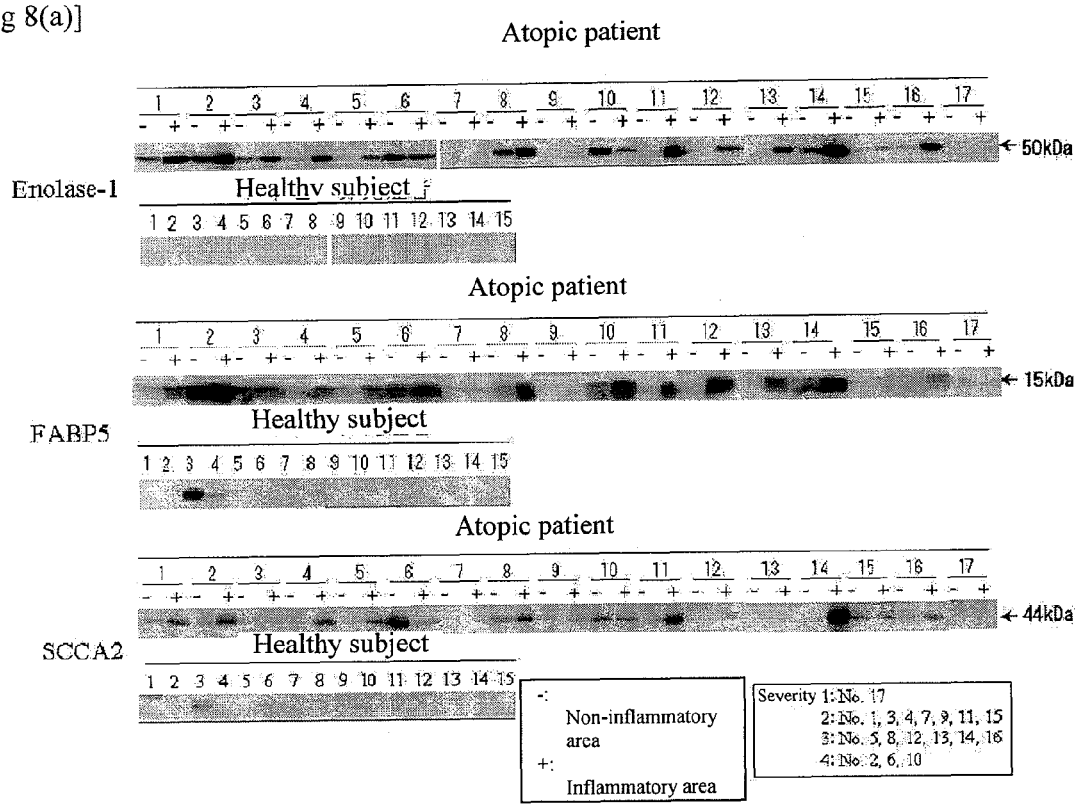
[Fig 8(b)]
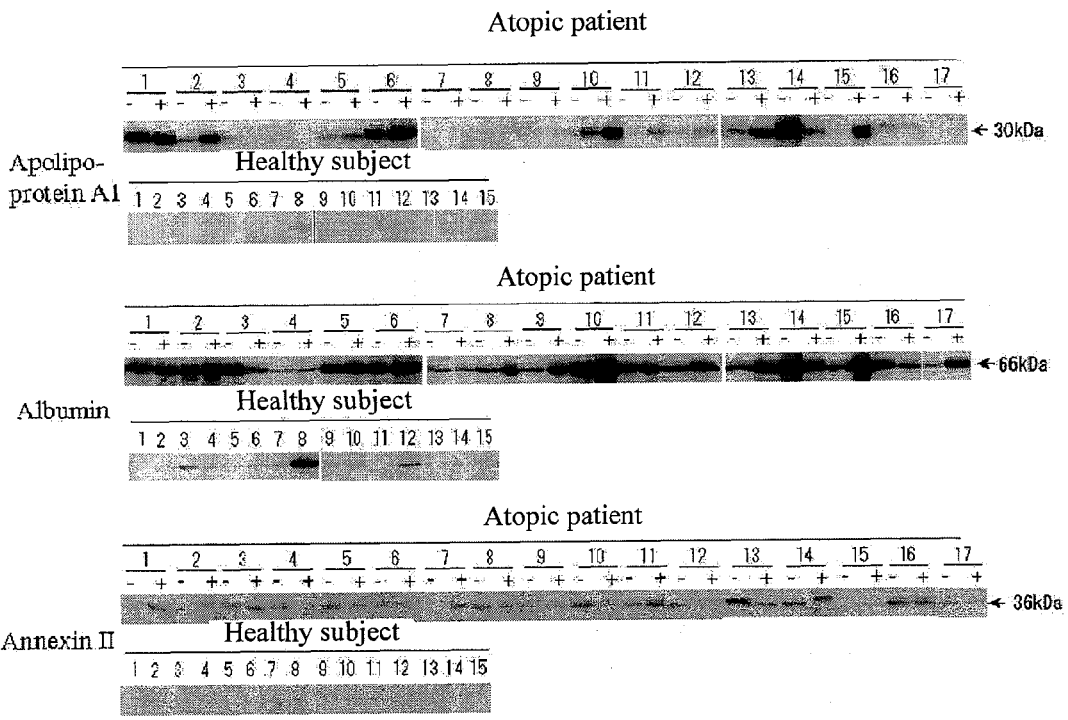

[Fig 9(a)]
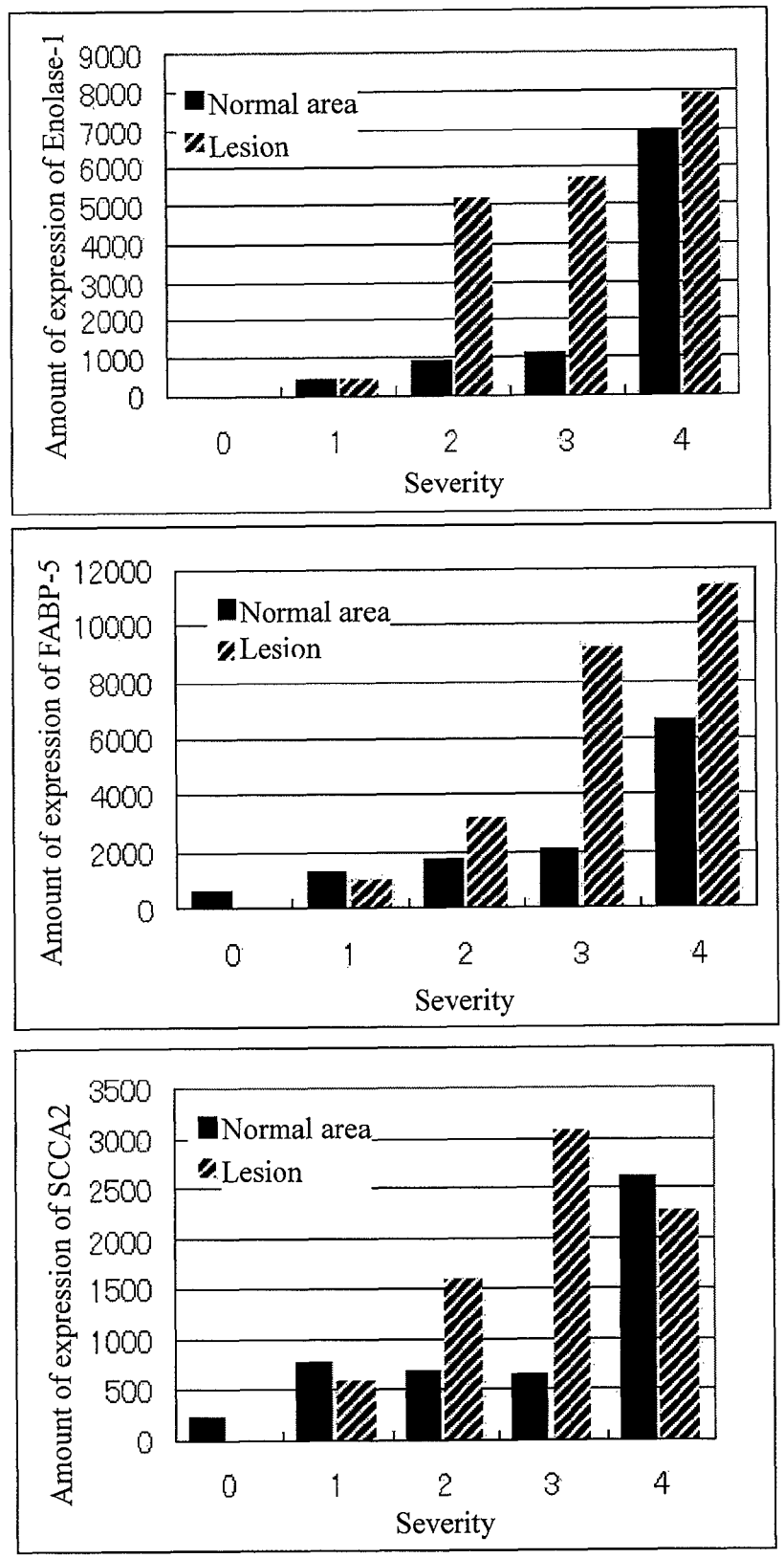

[Fig 9(b)]
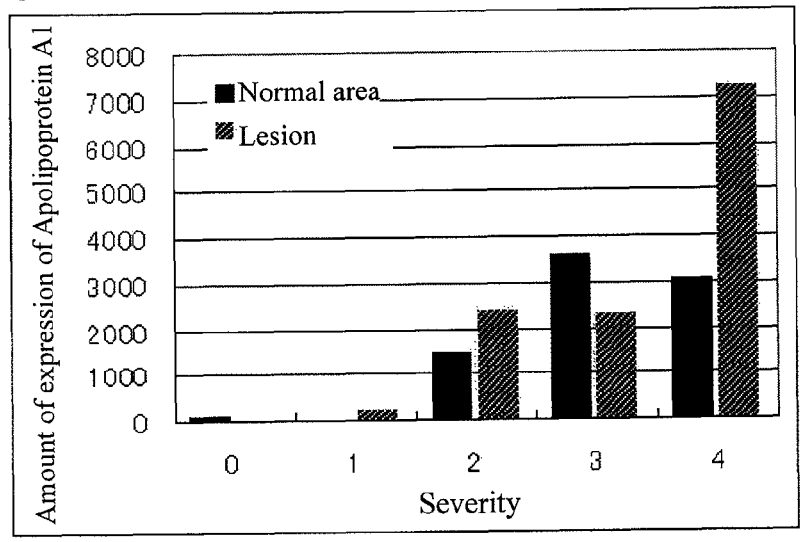
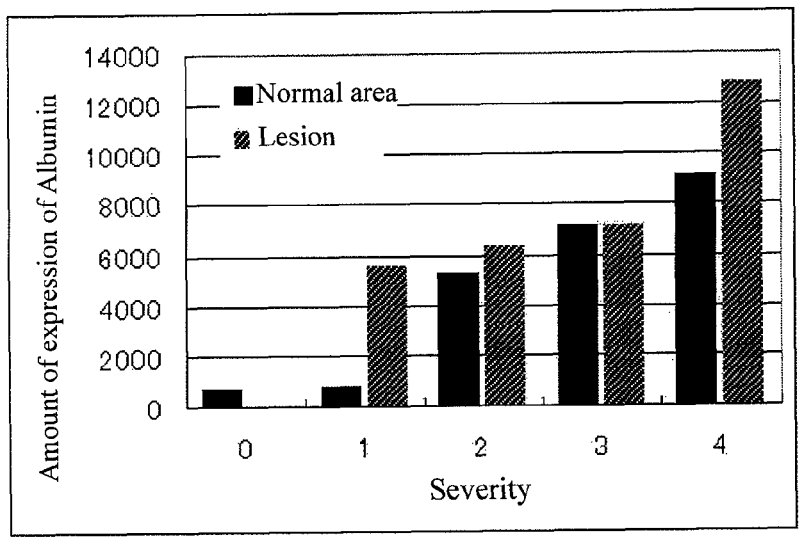
[Fig 10(a)]
Correlation of transepidermal weight loss and expression of FABP5
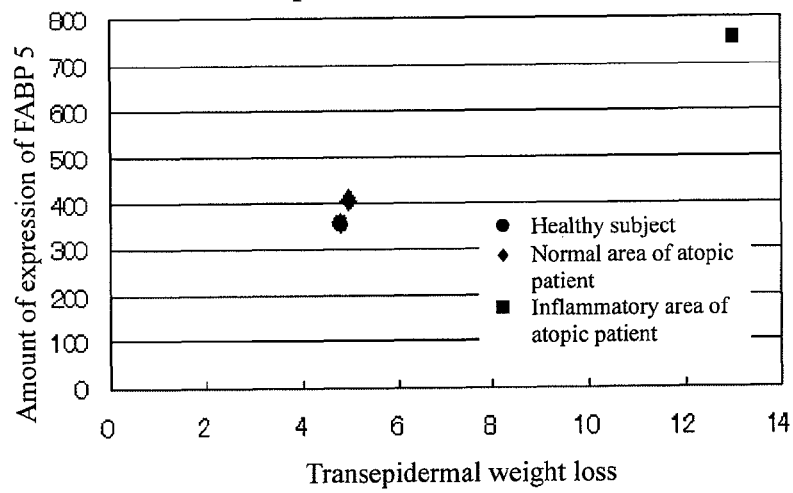

[Fig 10(b)]
Correlation of transepidermal weight loss and expression of Galectin 7
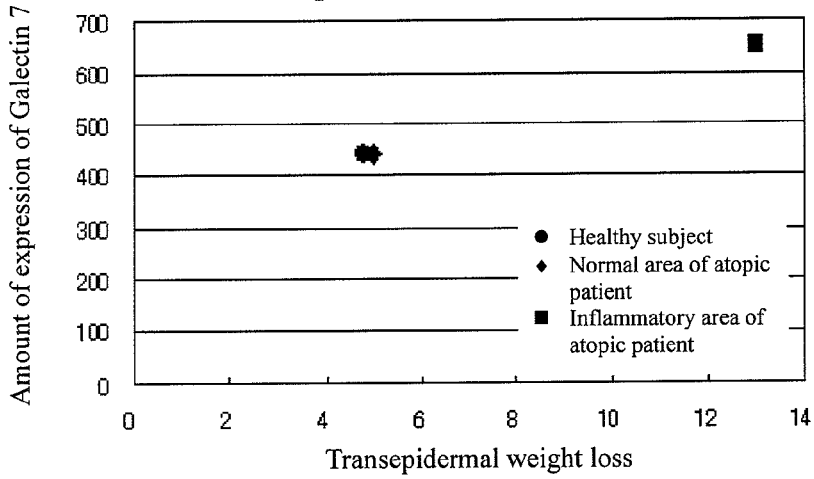
[Fig 10(c)]
Correlation of transepidermal weight loss and expression of Enolase 1
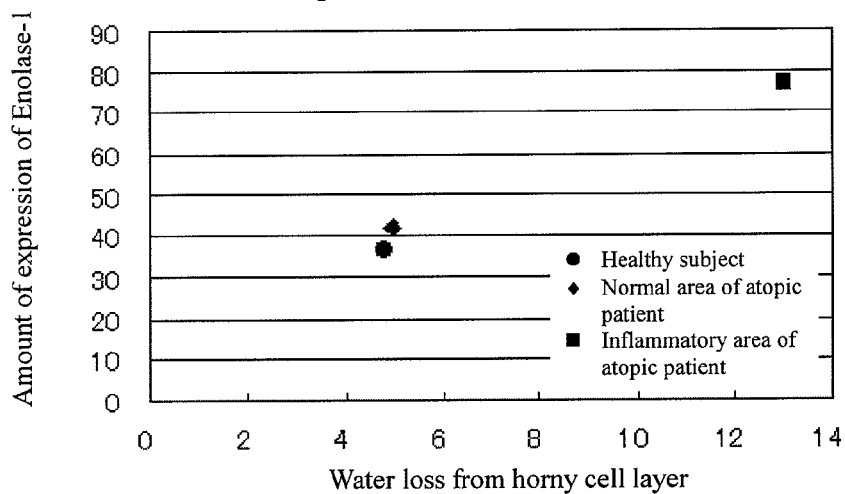
[Fig 10(d)]
Correlation of transepidermal weight loss and expression of SCCA2
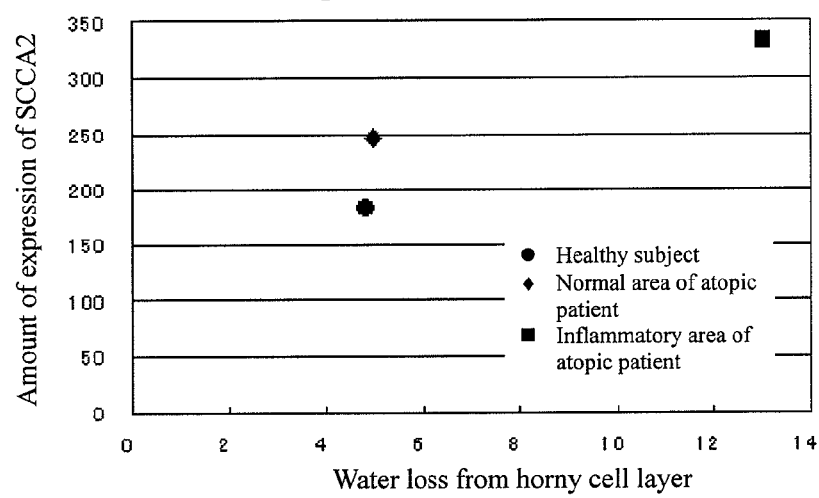

[Fig 10(e)]
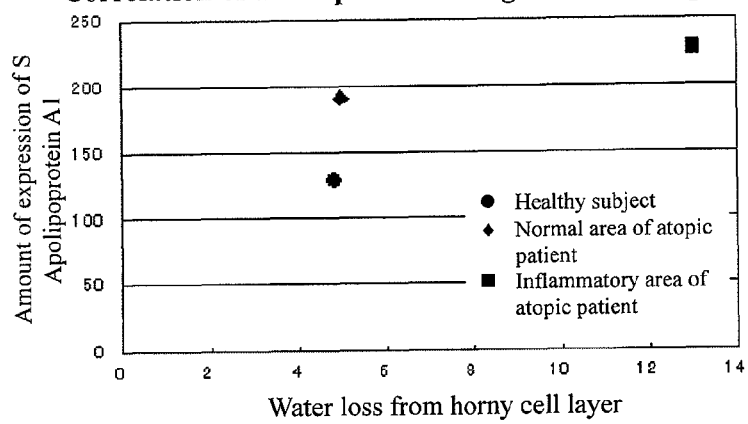
[Fig 10(f)]
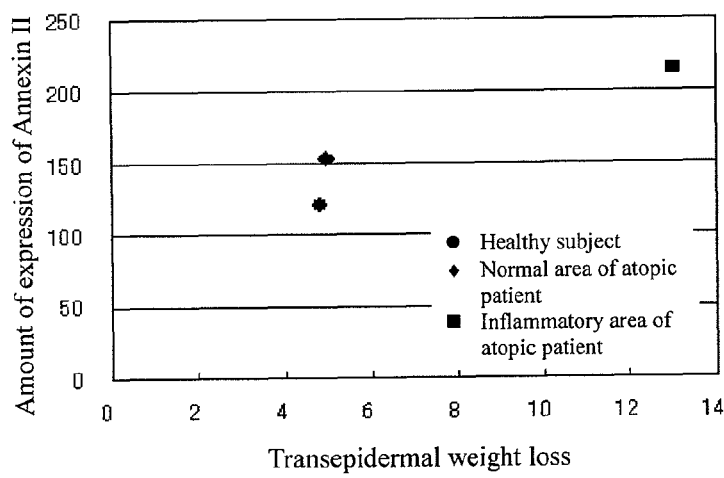
[Fig 11 (a)]
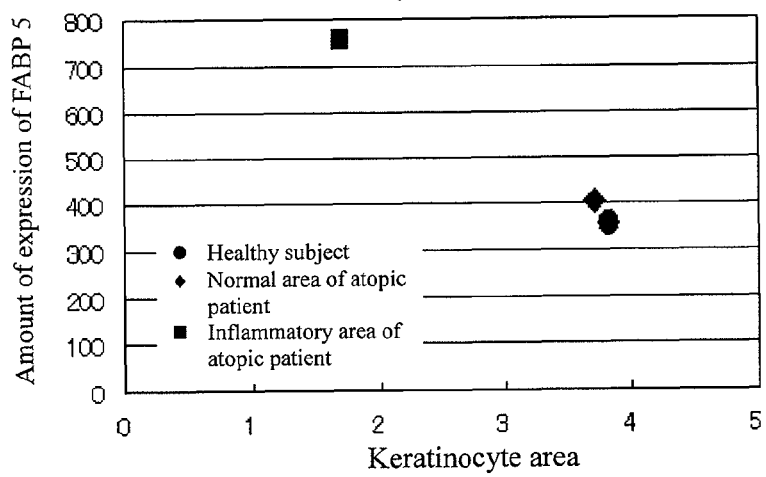

[Fig 11(b)]
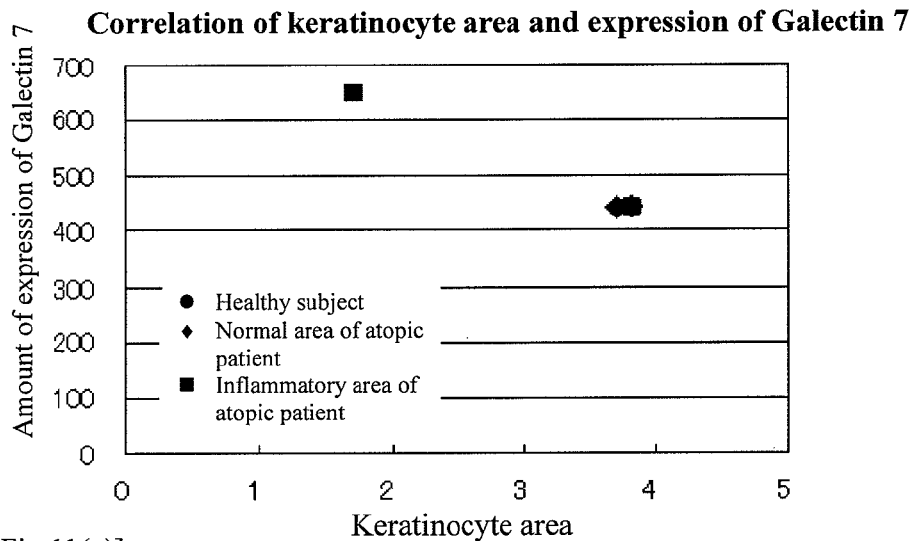
[Fig 11(c)]
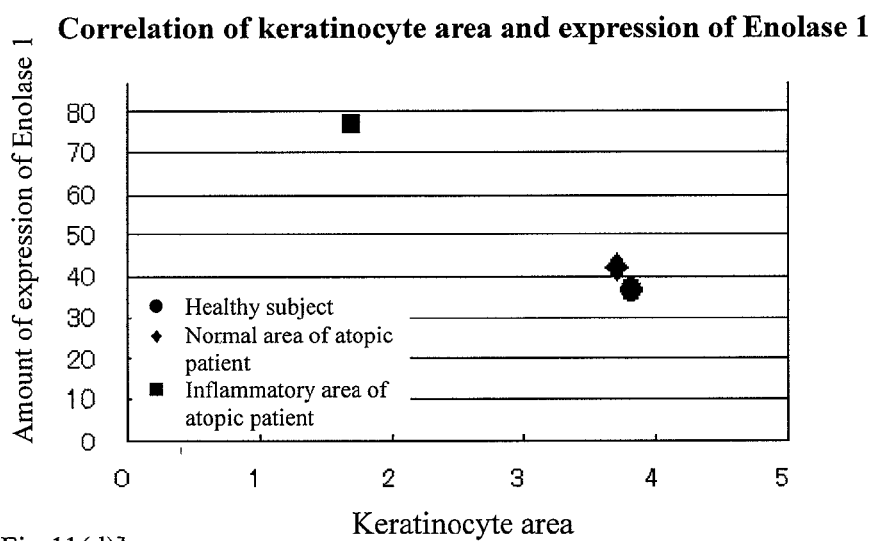
[Fig 11(d)]
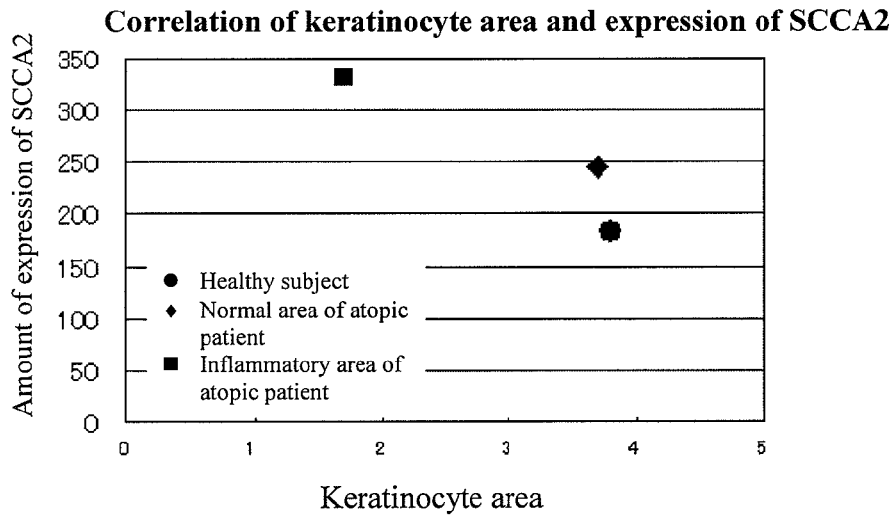

[Fig 11(e)]
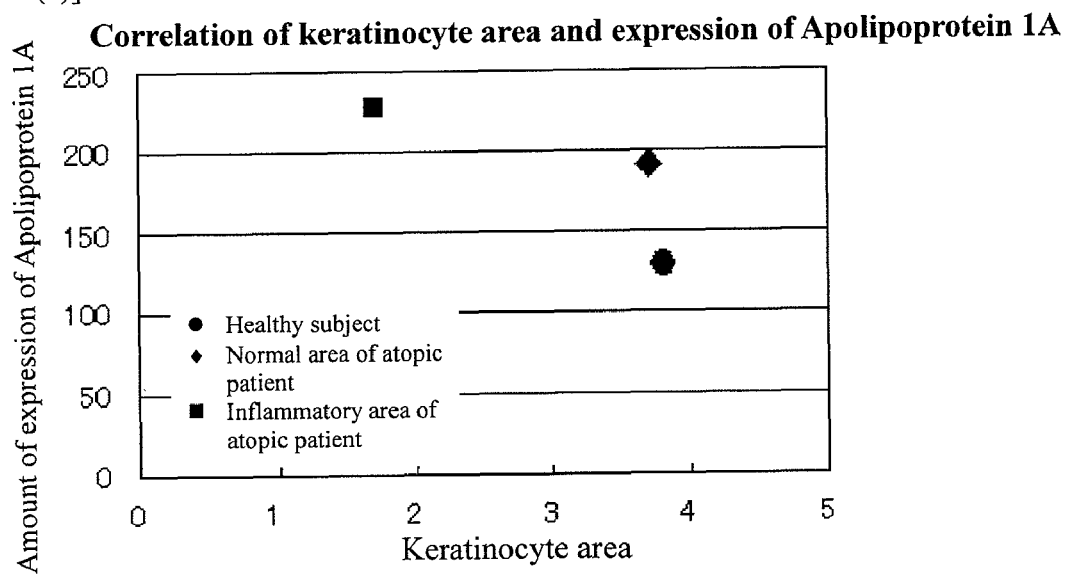
[Fig 11(f)]
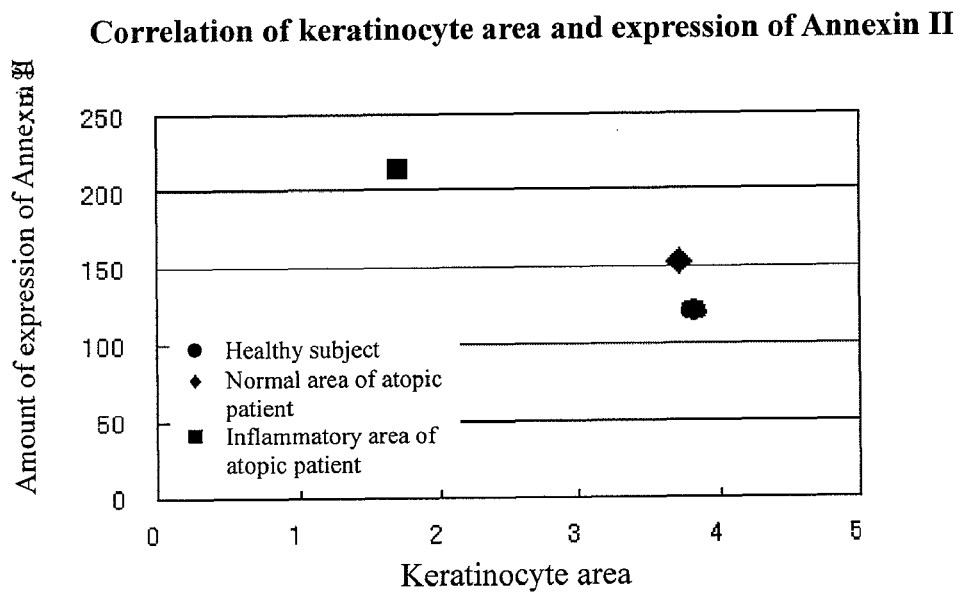

METHOD FOR DETERMINING ATOPIC DERMATITIS USING PROTEIN MARKER

This application is the U.S. National Phase under 35 U.S.C. §371 of International Application PCT/JP2006/320836, filed Oct. 19, 2006, which claims priority to Japanese Patent Application No. 2005-306498, filed Oct. 21, 2005. The International Application was published under PCT Article 21(2) in a language other than English.

FIELD OF TECHNOLOGY

The present invention relates to an atopic dermatitis marker and its utilization technology.

RELATED ART

Atopic dermatitis occurs for a variety of reasons including genetic factors and environmental factors, and the mechanism of how the condition occurs is not clear. Currently atopic dermatitis is diagnosed macroscopically and this diagnosis approach, which is affected by the subjective judgment of the clinician, is lacking objectivity. In particular, determination of the severity of exanthema to help determine a proper course of treatment of atopic dermatitis is presenting a difficult challenge. Also, there is a general current in society against use of steroid drugs for external use, which play a key role in the treatment of atopic dermatitis, and thus establishment of a proper treatment, as well as a proper dosage of each drug used, is desired. Accordingly, search for an atopic dermatitis marker that can be used to classify the degree of severity of atopic dermatitis as a measure of deterioration in condition, as an indicator of improvement, and also as a representation of effectiveness of treatment, presents an important challenge.

Currently IgE is used as an atopic dermatitis marker. However, conditions that cause the antibody titer of IgE to rise include asthma bronchiale, hepatic cirrhosis, etc., in addition to atopic dermatitis, and a high level of IgE antibody titer may not necessary be the result of atopic dermatitis. According to new information, expression of SCCA1 is shown to increase in the skin and blood of atopic dermatitis patients and thus a possible use of SCCA1 as a new biomarker is being suggested (Non-patent Literature 1). NGF, Substance P and IL-16 are also among the substances reported to be useful markers in the serum of atopic dermatitis patients (Non-patent Literatures 2 and 3). In addition, methods to comprehensively study biomarkers for atopic dermatitis using the skin taken from areas of inflammation caused by atopic dermatitis as well as non-inflammatory areas are being used. For example, applications for patent have been filed for disease markers that have been identified as genes relating to atopic dermatitis based on analysis of gene expressions using a DNA microarray (Patent Literatures 1 and 2). There are also separate reports that proteins extracted from cultures of epidermal keratinocytes and fibroblasts obtained from skin tissues of atopic dermatitis patients have been identified as atopic dermatitis markers using a mass spectrometer following a separation by means of two-dimensional electrophoresis (Non-patent Literatures 4 and 5).

However, there are no examples of proteome analysis using a protein in skin tissues taken from mice modeling atopic dermatitis. Also, all proteome analysis studies conducted to date on atopic dermatitis using human subjects involve a proteome analysis conducted after the initial culture of cells collected from the skin, which makes it difficult to conclude that the analysis results directly reflect the condition of atopic dermatitis in human.

Patent Literature 1: Japanese Patent Laid-open No. 2005-110602
Patent Literature 2: International Patent Publication No. WO01-065259
Non-patent Literature 1: Clin. Exp. Allergy 2005; 35: 1327-1333
Non-patent Literature 2: Br. J. Dermatol. 2002 July; 147 (1): 71-79
Non-patent Literature 3: Br. J. Dermatol. 2006 June; 154 (6): 1112-1117
Non-patent Literature 4: Proteomics 2004, 4, 3446-3455
Non-patent Literature 5: Proteomics 2006, 6, 1362-1370

SUMMARY OF THE INVENTION

Problems to Be Solved by the Invention

It is an object of the present invention to provide an objective marker for atopic dermatitis useful in both diagnosis and treatment. It is another object of the present invention to provide a method for screening components useful in the prevention or treatment of atopic dermatitis by utilizing such atopic dermatitis marker.

Means for Solving the Problems

The inventors applied haptene on mice (NC/Nga mice) modeling atopic dermatitis to artificially cause atopic dermatitis. At the same time, we used lactoferrin treatment, known to suppress atopic dermatitis, to suppress inflammation. The skin tissues obtained from those mice were then used to study proteins that changed due to development of atopic dermatitis. For the analysis method, proteome analysis involving two-dimensional electrophoresis (2-DE) and mass spectrometry (MS) was conducted and changes in identified proteins were checked using immuno-blotting.

As a result, FABP-5, Apolipoprotein A1, Vimentin, Rho GDI, etc., were identified as proteins whose expression increases with development of atopic dermatitis. On the other hand, Galectins such as Galectin-1, -3, -4, -7 and -8, cytoskeletal proteins such as Desmin, Moesin, Ezrin and Radixin, and Annexin II, Enolase 1, FABP-4, PARK7, HSP70, HSP90, etc., were identified as proteins whose expression decreases with development of atopic dermatitis. Many of these proteins showed an opposite change when treated with haptene and lactoferrin, suggesting that the increase or decrease in their expression has a good correlation with development of atopic dermatitis or lack thereof.

We also examined the correlation between the atopic dermatitis markers identified above and the degree of inflammation caused by atopic dermatitis in human by collecting samples of horny cell layer from volunteers including atopic dermatitis patients and healthy subjects using a horny cell layer checker, which is capable of collecting a sample of horny cell layer in a non-invasive, safe and simple manner, extracting proteins from the collected samples, and then examining expression of atopic dermatitis markers using the Western blotting method. As a result, it was found that Serum albumin, Immunoglobulin G, Annexin II, Apolipoprotein A1, FABP-5, Enolase 1 and Galectin-7 would increase their expression with an increase in the degree of inflammation caused by atopic dermatitis. On the other hand, Arginase I and Uracil-DNA glycosylase were identified as proteins whose expression decreases with an increase in the degree of inflammation caused by atopic dermatitis.

The key points of the present invention are specified below.
1. A method for determining atopic dermatitis, including measurement of the expression of specific proteins listed below and/or their genes in skin cells and/or skin tissues; wherein the specific proteins change their expression with inflammation caused by atopic dermatitis.
   The specific proteins are the following 23 types:
   (1) a protein selected from a group of Gelactins consisting of Galectin-1, Galectin-3, Galectin-4, Galectin-7 and Galectin-8;
   (2) a protein selected from a group of HSPs consisting of HSP70 and HSP90;
   (3) a protein selected from a group of cytoskeletal proteins consisting of Vimentin, Rho GDI, Desmin, Moesin, Ezrin and Radixin;
   (4) a protein selected from a group of FABPs consisting of FABP-4 and FABP-5; and
   (5) other proteins including Serum albumin, Immunoglobulin G, Annexin II, Apolipoprotein A1, Enolase 1, PARK7, Arginase I and Uracil DNA glycosylase.
2. A method according to 1, wherein the skin cells and/or skin tissues are those of the skin's horny cell layer collected using a horny cell layer checker.
3. A method according to 1, wherein the expression of specific proteins is measured at the protein level.
4. A method according to 1, wherein the expression of genes of specific proteins is measured at the RNA level.
5. A kit for determining atopic dermatitis, including reagents capable of measuring the expression of specific proteins listed below in skin cells and/or skin tissues; wherein the specific proteins change their expression with inflammation caused by atopic dermatitis.
   The specific proteins are the following 23 types:
   (1) a protein selected from a group of Gelactins consisting of Galectin-1, Galectin-3, Galectin-4, Galectin-7 and Galectin-8;
   (2) a protein selected from a group of HSPs consisting of HSP70 and HSP90;
   (3) a protein selected from a group of cytoskeletal proteins consisting of Vimentin, Rho GDI, Desmin, Moesin, Ezrin and Radixin;
   (4) a protein selected from a group of FABPs consisting of FABP-4 and FABP-5; and
   (5) other proteins including Serum albumin, Immunoglobulin G, Annexin II, Apolipoprotein A1, Enolase 1, PARK7, Arginase I and Uracil DNA glycosylase.
6. A kit according to 5, comprising a horny cell layer checker for collecting skin cells and/or skin tissues.
7. A kit according to 5, wherein the reagents are antibodies capable of specifically recognizing the specific proteins whose expression changes with inflammation caused by atopic dermatitis.
8. A kit according to 5, wherein the reagents are nucleic acid probes capable of specifically hybridizing with mRNA of the specific proteins whose expression changes with inflammation caused by atopic dermatitis.
9. A kit according to 5, wherein the reagents are a pair of nucleic acid primers including a nucleic acid primer capable of specifically hybridizing with mRNA of the specific proteins whose expression changes with inflammation caused by atopic dermatitis, and a nucleic acid primer capable of specifically hybridizing with cDNA synthesized using the aforementioned mRNA as a mold.
10. A method for identifying substances effective in the treatment and/or prevention of atopic dermatitis, including:
    (a) a step to cause a target substance to contact skin cells and/or skin tissues;
    (b) a step to culture for a specified time the skin cells and/or skin tissues contacted by the target substance in step (a);
    (c) a step to measure the expression of specific proteins listed below and/or their genes in the skin cells and/or skin tissues cultured in step (b), wherein the specific proteins change their expression with inflammation caused by atopic dermatitis; and
    (d) a step to evaluate the effects of the target substance on the expression of the specific proteins and/or their genes in skin cells and/or skin tissues, by comparing the expression of the specific proteins and/or their genes measured in step (c) against the expression of the specific proteins and/or their genes in control skin cells and/or skin tissues.
    The specific proteins are the following 23 types:
    (1) a protein selected from a group of Gelactins consisting of Galectin-1, Galectin-3, Galectin-4, Galectin-7 and Galectin-8;
    (2) a protein selected from a group of HSPs consisting of HSP70 and HSP90;
    (3) a protein selected from a group a group of cytoskeletal proteins consisting of Vimentin, Rho GDI, Desmin, Moesin, Ezrin and Radixin;
    (4) a protein selected from a group of FABPs consisting of FABP-4 and FABP-5; and
    (5) other proteins including Serum albumin, Immunoglobulin G, Annexin II, Apolipoprotein A1, Enolase 1, PARK7, Arginase I and Uracil DNA glycosylase.

Effects of the Invention

The present invention can be used to establish an evaluation system for diagnosing atopic dermatitis and measuring the severity thereof. By using this evaluation system, the severity of atopic dermatitis and risk of developing the condition can be determined more objectively than when conventional methods are used. In addition, a kit for determining the severity of atopic dermatitis and risk of developing the condition, and a method for identifying components effective in the suppression of inflammation caused by atopic dermatitis, are also provided.

BRIEF DESCRIPTION OF THE DRAWINGS

[FIG. 1] Skin conditions of mice tested under four experimental conditions ((1) haptene (−)/lactoferrin (−), (2) haptene (−)/lactoferrin (+), (3) haptene (+)/lactoferrin (−), (4) haptene (+)/lactoferrin (+))

[FIG. 2A] Results of two-dimensional electrophoresis using skin tissues of mice modeling atopic dermatitis (tested under the experimental conditions of haptene (−)/lactoferrin (−) and haptene (+)/lactoferrin (−))

[FIG. 2B] Results of two-dimensional electrophoresis using skin tissues of mice modeling atopic dermatitis (tested under the experimental conditions of haptene (−)/lactoferrin (+) and haptene (+)/lactoferrin (+))

[FIG. 3] Changes in Galectin expressions occurring in skin tissues of mice modeling atopic dermatitis

[FIG. 4] Changes in cytoskeletal protein and HSP protein expressions occurring in skin tissues of mice modeling atopic dermatitis

[FIG. 5] Changes in protein expressions in skin tissues of mice modeling atopic dermatitis

[FIG. 6] Results of identification, using a mass spectrometer (MALDI TOF-MS), of proteins whose expression increased in samples exhibiting atopy

[FIG. 7] Changes in protein expressions occurring in skin tissues of atopic dermatitis patients

[FIG. 8A, 8B] Correlations between severity of atopic dermatitis and amount of protein expression in atopic dermatitis patients

[FIG. 9A, 9B] Results of quantification of expression intensities, in each sample, of five marker proteins including Enolase 1, FABP-5, SCCA2, Apolipoprotein A1 and Serum albumin, summarized by severity of patient's condition

[FIG. 10A to 10F] Correlations between amount of transepidermal water loss and marker expression in healthy subjects and subjects with a history of atopic dermatitis

[FIG. 11A to 10F] Correlations between keratinocyte area and marker expression in healthy subjects and subjects with a history of atopic dermatitis

BEST MODE FOR CARRYING OUT THE INVENTION

Embodiments of the present invention are explained below in details.

The present invention provides a method for determining atopic dermatitis, including measurement of the expression of specific proteins and/or their genes in skin cells and/or skin tissues. These specific proteins change their expression with inflammation caused by atopic dermatitis.

Patterns in which "expression changes" include, among others, change in presence or absence of expression of a protein and/or its gene, and increase or decrease in the amount of expression. The specific proteins should ideally be selected from a group consisting of Apolipoprotein A1, FABP-4, FABP-5, Vimentin, Rho GDI, Annexin II, Enolase 1, Galectin-1, Galectin-3, Galectin-4, Galectin-7, Galectin-8, PARK7, Desmin, Moesin, Ezrin, Radixin, HSP70, HSP90, Serum albumin, Immunoglobulin G, Arginase I and Uracil-DNA glycosylase. One or more of these proteins can be selected.

The aforementioned 23 types of specific proteins are classified as follows:

(1) a protein selected from a group of Gelactins consisting of Galectin-1, Galectin-3, Galectin-4, Galectin-7 and Galectin-8;
(2) a protein selected from a group of HSPs consisting of HSP70 and HSP90;
(3) a protein selected from a group of cytoskeletal proteins consisting of Vimentin, Rho GDI, Desmin, Moesin, Ezrin and Radixin;
(4) a protein selected from a group of FABPs consisting of FABP-4 and FABP-5; and
(5) other proteins including Serum albumin, Immunoglobulin G, Annexin II, Apolipoprotein A1, Enolase 1, PARK7, Arginase I and Uracil DNA glycosylase.

Apolipoprotein A1 is a secretory protein with a molecular weight of 30,778 Da. It serves to promote the outflow of cholesterol from tissues and transport cholesterol back to the liver. This secretory protein is present in a large amount in chylomicron and plasma HDL, and is known to express in psoriatic skin tissues (characterized by regular thickness increase and parakeratosis of skin). Gene sequence information (Apolipoprotein A1, Nucleic Acids Res. 11: 2827-2837 (1983), P02647). Amino acid sequence information (Apolipoprotein A1, Biochem. Biophys. Res. Commun. 80: 623-630 (1978), M27875).

FABP-5 (Fatty acid binding protein-5) is an intracellular protein with a molecular weight of 15,033 Da. This protein is present mainly in the epidermis and was initially identified due to a rise in its expression in psoriatic skin tissues (characterized by regular thickness increase and parakeratosis of skin). The intracellular protein bonds with a fatty acid (oleic acid) and hydrophobic ligands and is involved in the intake, transport and metabolism of fatty acid as well as proliferation and differentiation of cells. Although FABP-5 does not express much in proliferating epidermal keratinocytes, its expression increases to around double as a result of induced differentiation. FABP-5 also bonds with S100A7 (a calcium-dependent signaling protein) expressed prominently in psoriatic skin, and is also located in the focal adhesion structure in the differentiation stage of epidermal keratinocytes. Gene sequence information (Fatty acid binding protein 5, J. Invest. Dermatol. 99: 299-305 (1992), BC070303). Amino acid sequence information (Fatty acid-binding protein, epidermal, Biochem. J. 302: 363-371 (1994), Q01469).

Vimentin is a cytoskeletal protein with a molecular weight of 53,520 Da. This protein constitutes an intermediate filament of Class III type. Vimentin is distributed in a net-like pattern over a wide range of many mesenchymal cells, and makes cells stronger against mechanical stress received from the outside world. The structure of Vimentin is adjusted as a result of phosphorylation. Existence of binding proteins such as plectin and synemin is also known. Gene sequence information (Vimentin, Nucleic Acids Res. 18: 6692-6692 (1990), M14144). Amino acid sequence information (Vimentin, Electrophoresis 18: 588-598 (1997), P08670).

Rho GDI (Rho GDP-dissociation inhibitor 1) is an intracellular protein with a molecular weight of 23,207 Da. It is expressed prominently when epidermal keratinocytes differentiate. Rho GDI inhibitively adjusts the conversion of Rho protein from GDP type to GTP type. Accordingly, forced expression of Rho GDI in cells causes stress fibers, focal adhesions, etc., to disappear and actin skeletal systems in cells to collapse. Gene sequence information (Rho GDP-dissociation inhibitor 1, Exp. Cell Res. 209: 165-174 (1993), X69550). Amino acid sequence information (Rho GDP-dissociation inhibitor, P52565).

Annexin II is an intracellular protein with a molecular weight of 38,473 Da. There are reports that Annexin II is partially secreted extracellularly. It is a membrane-binding protein controlled by calcium and two calcium ions bond with this protein. Annexin II is located near cell membranes. Of the two pairs of Annexin repeats, one bonds with calcium and the other bonds with phospholipids. This protein cross-links with actins bonded to phospholipids in cell membranes as well as with cytoskeletal proteins, and activates plasminogen via t-PA (tissue Plasminogen Activator). Gene basal sequence information (Annexin A2, Gene 95: 243-251 (1990), BC015834). Amino acid sequence information (Annexin A2, J. Biol. Chem. 266: 5169-5176 (1991), P07355).

Enolase 1 is an intracellular protein with a molecular weight of 47,038 Da. It has an enzyme activity of 2-phospho-D-glycerate=phosphoenolpyruvate+$H_2O$ and functions in the glycolysis system. There are also reports that Enolase 1 is involved in cell proliferation and allergy. It controls the activation of plasminogen at the cell surface of leukocytes and nerves and is involved in the formation of fibrins. Magnesium is needed for Enolase 1 to have a stable dimer structure. Although Enolase 1 is located in cytoplasm, its homodimer form is also seen in cell membranes. α-enolase is expressed in almost all tissues, while β-enolase and γ-enolase are expressed only in muscle tissues and nerve tissues, respectively. Gene sequence information (Alpha enolase, Proc. Natl. Acad. Sci. USA. 83: 6741-6745 (1986), M14328). Amino acid sequence information (Alpha enolase, Enzyme Protein 48: 37-44 (1995), P06733).

Galectin-1 is an intracellular protein with a molecular weight of 14,585 Da. It is partially secreted extracellularly. Galectin-1 is present in the heart, stomach, skeletal muscles, nerves, thymus gland, kidney, placenta, etc. It bonds with β-galactoside, CD45, CD3, CD4, etc. Galectin-1 is known to be effective in promoting cell proliferation, induce apoptosis, and affect immune response. It also specifically bonds with Laminin, Integrin and other extracellular matrix components and cell receptors and has significant impact on the bonding and movement of cells. Gene sequence information (Galectin-1, J. Biol. Chem. 264: 1310-1316 (1989), BT006775). Amino acid sequence information (Galectin-1, J. Biochem. 104: 1-4 (1988), P09382).

Galectin-3 is an intracellular protein with a molecular weight of 35,678 Da. It is a galactose-specific lectin that bonds with IgE. Its expression is mainly found in the epidermis of large intestine and also in active macrophages. Galectin-3 is produced by epidermal keratinocytes and present in the surface of islet of Langerhans, and is reportedly controlling the immune system by bonding with IgE. Gene sequence information (Galectin-3, Proc. Natl. Acad. Sci. USA. 87: 7324-7328 (1990), AB006780). Amino acid sequence information (Galectin-3, P17931).

Galectin-4 is an intracellular protein with a molecular weight of 35,941 Da. Galectin-4 is isolated from T84, which is a colon cancer cell strain, and present in the bond between a cell and a matrix, as well as in the bond between cells. Gene sequence information (Galectin-4, Eur. J. Biochem. 248: 225-230 (1997), AB006781). Amino acid sequence information (Galectin-4, P56470).

Galectin-7 is an intracellular protein with a molecular weight of 14,944 Da. In general, Galectin-7 controls the cell proliferation between cells and between a cell and an extracellular matrix. Galectin-7 is an apoptosis-related protein that controls the activity of JNK and release of cytochrome C. It is also secreted to the cytoplasm, nucleus, and outside the cell. Galecin-7 is a member of the Galectin sub-family, which is the first to have been cloned among proteins found in human epidermis. Studies of cultured epidermal keratinocytes show that Galectin-7 is not affected by the degree of cornification and is expressed in all epidermal cells. Gene sequence information (Galectin-7, Dev. Biol. 168: 259-271 (1995), L07769). Amino acid sequence information (Galectin-7, J. Biol. Chem. 270: 5823-5829 (1995), P47929).

Galectin-8 is an intracellular protein with a molecular weight of 35,539 Da. Galectin-8 is expressed in a wide range of tissues in the liver, heart, muscles, kidney and brain, among others. It is expressed specifically in prostate cancer cells and not found in normal prostates and benign growths. Although Galectin-8 is little present in embryos, its expression is very high in adult tissues. Gene sequence information (Galectin-8, Proc. Natl. Acad. Sci. USA. 93: 7252-7257 (1996), X91790). Amino acid sequence information (Galectin-8, 000214).

PARK7 is an intracellular protein with a molecular weight of 19,891 Da. PARK7 was initially identified as a protein relating to Parkinson's disease, but later revealed to be involved in re-epithelialization that occurs as a wound in skin heals. Judging from its solid structure, PARK7 is also suggested to be functioning as a protease. Gene sequence information (Parkinson disease 7, Biochem. Biophys. Res. Commun. 231: 509-513 (1997), BC008188). Amino acid sequence information (DJ-1 protein, Q99497).

Desmin is a cytoskeletal protein with a molecular weight of 53,405 Da. It is a type of Class III intermediate filament having a hand in the retention of structure and strength of cells. Being a fibrous polypeptide polymer, Desmin is present in smooth muscles and striated muscles. Gene sequence information (Desmin, Gene 78: 243-254 (1989), U59167). Amino acid sequence information (Desmin, P17661).

Ezrin is an intracellular protein with a molecular weight of 69,268 Da. Moesin and Radixin mentioned below belong to the same family as Ezrin. Ezrin mainly serves to connect cytoskeletal proteins to cell membranes. It is located inside filiform projections on cell membranes called "microvilli." Ezrin constitutes microvilli in intestinal epithelial cells. It is phosphorylated by tyrosine kinase. Gene sequence information (Ezrin, J. Biol. Chem. 264: 16727-16732 (1989), X51.521). Amino acid sequence information (Ezrin, Biochem. Biophys. Res. Commun. 224: 666-674 (1996), P15311).

Radixin is an intracellular protein with a molecular weight of 68,564 Da. It mainly serves to connect cytoskeletal proteins to cell membranes. Gene sequence information (Radixin, Genomics 16: 199-206 (1993), L02320). Amino acid sequence information (Radixin, P35241).

Moesin is an intracellular protein with a molecular weight of 67,689 Da. It mainly serves to connect cytoskeletal proteins to cell membranes. There are reports that the expression of Moesin decreases in abnormally differentiated epidermal keratinocytes. Gene sequence information (Moesin, Proc. Natl. Acad. Sci. USA. 88: 8297-8301 (1991), M69066). Amino acid sequence information (Moesin, Proc. Natl. Acad. Sci. USA. 88: 8297-8301 (1991), P26038).

FABP-4 (Fatty acid binding protein-4) is an intracellular protein with a molecular weight of 14,588 Da. It transports lipids to fat cells. FABP-4 mainly bonds with fatty acids and retinoic acids in cells. Its expression increases according to the differentiation stage of fat cells. FABP-4 has a high homology with FABP-5. Gene sequence information (Fatty acid-binding protein, adipocyte, Biochemistry 28: 8683-8690 (1989), BT006809). Amino acid sequence information (Fatty acid-binding protein, adipocyte, P15090).

HSP70 (Heat shock protein 70) is an intracellular protein with a molecular weight of 70,052 Da. Normally it functions as a molecular chaperon in cells and is involved in the folding, transport, aggregation and breakdown of proteins, among others. In mitochondria and ER, HSP70 serves to correctly transfer proteins. HSP70 coordinates with HSP90 to play a role in signal transmission in cells. Gene basal sequence information (Heat shock 70 kDa protein 1A, Immunogenetics 32: 242-251 (1990), BC002453). Amino acid sequence information (Heat shock 70 kDa protein 1, P08107).

HSP90 (Heat shock protein 90) is an intracellular protein with a molecular weight of 85,453 Da. When cells are exposed to high temperature, HSP90 changes its structure and functions as a molecular chaperon to prevent irreversible denaturing of other proteins. In certain types of cells, HSP90 is reportedly involved in signal transmission. Gene basal sequence information (Heat shock protein 90, Nucleic Acids Res. 17: 7108-7108 (1989), X15183). Amino acid sequence information (Heat shock protein 90, J. Biol. Chem. 264: 2431-2437 (1989), P07900).

Serum albumin is a secretory protein with a molecular weight of 69,367 Da, found in a large amount in serum. The basic functions of Serum albumin are maintenance of colloid osmotic pressure of blood and support/transport of various substances. Gene sequence information (Serum albumin, Proc. Natl. Acad. Sci. USA. 79: 71-75 (1982), V00494). Amino acid sequence information (Serum albumin, FEBS Lett. 58: 134-137 (1975), P02768).

Immunoglobulin G (IgG) is a secretory protein with a molecular weight of 42,632 Da. It accounts for 75% of the entire immunoglobulin population in the human body. The bioactivities of IgG include activation of complements, enhancement of intake into macrophages, and facilitation of passage through the placenta. On the other hand, IgG is expressed by a genetic class switch at a large sub-unit (H chain) of Immunoglobulin IgG. IgG is present in a large amount in serum and its half period is also long. IgG forms various antibody molecules with light chains (L chains) and plays a central role in immune response. Gene sequence information (Immunoglobulin gamma, Nucleic Acids Res. 16: 11824-11824 (1988), X14356). Amino acid sequence information (Immunoglobulin gamma, Protein Sci. 13: 2819-2824 (2004), P12314).

Arginase I is an intracellular protein with a molecular weight of 34,735 Da. It is a unidirectional reaction enzyme that hydrolyzes L-arginin into L-ornithine and urea. Although Arginase I is located in the liver, small amounts are also found in the kidney, brain, mammary gland and skin. Lack of Arginase I causes argininemia, which leads to mental retardation and spastic quadriplegia. Gene sequence information (Arginase type I, Proc. Natl. Acad. Sci. USA. 84: 412-415 (1987), AY074488). Amino acid sequence information (Arginase-1, P05089).

Uracil-DNA glycosylase is an intracellular protein with a molecular weight of 34,645 Da.

When cytosine in DNA undergoes deamination, it becomes uracil and forms a base pair with adenine to induce mutation. Uracil-DNA glycosylase is an enzyme having the effect of preventing this mutation by hydrolyzing the N-glycosyl bond of deoxyuridine produced by deamination. Two isoforms are present. Isoform I is located in mitochondria in cells, and its distribution is also found in muscle tissues. Isoform II is expressed in a large amount in the nucleuses of tissue cells that are proliferating. Gene sequence information (Uracil-DNA glycosylase, EMBO J. 8: 3121-3125 (1989), X15653). Amino acid sequence information (Uracil-DNA glycosylase, EMBO J. 8: 3121-3125 (1989), P13051).

The above proteins may be a precursor protein or mature protein, or of severed type or non-severed type. Examples of precursor proteins include pro-proteins and prepro-proteins, among others. Some pro-proteins and prepro-proteins have a signal peptide.

Under the method proposed by the present invention, expression of a specific protein may be measured in skin cells and/or skin tissues, or expression of its gene may be measured. For example, such measurement can be performed using the Northern blotting method, RT-PCR method, Western blotting method, immunohistochemical analysis method, ELISA method, antibody chip, cDNA micro-array, FRET (Fluorescence Resonance Energy Transfer) method, etc.

To measure expression of specific proteins at the protein level, it is effective to use an antibody that specifically recognizes the target protein. This antibody may be a monoclonal antibody or polyclonal antibody. These antibodies can be manufactured by known methods and some are commercially available. If the Western blotting method is used to perform measurement, the antibody is secondarily detected using $^{125}$I labeled protein A, peroxidase-binding IgG, etc. If measurement is performed using the immunohistochemical analysis method, ideally the antibody should be labeled with a fluorochrome, ferritin, enzyme, etc.

To measure gene expression of specific proteins at the RNA level, it is effective to use a nucleic acid probe capable of specifically hybridizing with mRNA of the target protein (if the Northern blotting method is used to perform measurement). Alternatively, a pair of nucleic acid primers may be used, including a nucleic acid primer specifically hybridizing with mRNA of the target protein, and a nucleic acid primer capable of specifically hybridizing with cDNA synthesized using the aforementioned mRNA as a mold (if the PCR method is used to perform measurement). Nucleic acid probes and primers can be designed based on the gene information of the target protein. Normally, nucleic acid probes having a basicity of approx. 15 to 1500 are appropriate. Ideally nucleic acid probes should be labeled with a radioactive element, fluorochrome, enzyme, etc. Normally, nucleic acid primers having a basicity of approx. 15 to 30 are appropriate.

Under the present invention, presence/absence of expression of specific proteins or their genes in skin cells and/or skin tissues may be detected or the amount of expression may be measured.

Presence/absence of expression of proteins and/or their mRNA can be checked from presence/absence of appearance of spots and bands at specified locations. The amount of expression of proteins and/or their mRNA can be measured using the staining intensity of spots and bands. Alternatively, proteins and/or their mRNA may be quantified. To measure multiple gene expressions or multiple protein expressions simultaneously, use of such detection methods as DNA array (with the probe fixed on the substrate) (Nature Reviews, Drug Discovery, Volume 1, December 2002, 951-960), protein chip (with the antibody fixed on the substrate) (Nature Reviews, Drug Discovery, Volume 1, September 2002, 683-695), and Luminex (Nature Reviews, Drug Discovery, Volume 1, June 2002, 447-456), is preferred.

Skin cells and skin tissues should ideally be derived from the test subject. Examples of life forms that may become test subjects include human, pig, monkey, chimpanzee, dog, cow, rabbit, rat, mouse and other mammals.

Under the method proposed by the present invention, skin biopsy samples, or cultured skin cells, cultured skin tissues and the like, obtained from skin biopsy samples, can be used to determine atopic dermatitis. Skin biopsy samples may be collected from the skin's horny cell layer using a tape (horny cell layer checker) as described later in examples.

Examples of skin cells include epidermal keratinocytes, skin fibroblasts, Langerhans cells, melanin cells, mast cells, endothelial cells, sebum cells, hair papilla cells and hair matrix cells, among others. Skin cells can be collected from the skin using known methods (*Bunshi Seibutsugaku Kenkyu no Tameno Shin Saibobaiyo Jikkenho* (New Experimental Cell Culture Methods for Molecular Biology Research), p. 57-71, Yodosha, 1999).

Examples of skin tissues include horny cell layer, epidermis and dermis of skin, among others. Skin tissues can be collected from the skin using known methods (Acta. Derm. Venereol., 85, 389-393, 2005).

Skin biopsy samples may be cells or tissues. Skin biopsy samples should ideally be those of the skin's horny cell layer collected by a horny cell layer checker or other tapes, as described later in examples. Horny cell layer checkers measure the degree of parakeratosis and cell area of the horny cell layer, and have been used for many years in the collection of samples of horny cell layer for the purpose of evaluating the degree of skin roughness and turnover rate of horny cell layer (*Keshohin no Yuyosei: Hyoka Gijutsu no Shimpo to Shorai Tembo* (Utility of Cosmetics: Progress and Future Perspective of Evaluation Technologies), Society of Cosmetic Chemists of Japan, Yakuji Nippo, p95-96). These checkers are very useful in collecting samples from the horny cell layer in a non-invasive, easy and safe manner at a counseling outlet or home.

In an example of the present invention, atopic dermatitis can be determined using the standards explained below.

As shown in Example 1 (FIG. 8), where various antibodies are used to analyze Enolase 1, FABP-5, SCCA2, Apolipoprotein A1, Albumin and Annexin II, among others, skin samples were obtained from volunteer subjects suffering from atopic dermatitis and the amount of expression was measured for several types of marker proteins or their genes to reveal the relationship between the condition of this disease and the amount of expression.

The degree of condition of atopic dermatitis and cause of its development are determined using analysis samples by comparing the affected areas (analysis samples) and non-affected areas (patient control samples) of atopic dermatitis patients and the corresponding areas of subjects not suffering from atopic dermatitis (non-patient control samples). This way, analysis results of marker proteins can be utilized in the diagnosis and treatment of atopic dermatitis that manifests in a variety of conditions.

The present invention also provides a kit for determining atopic dermatitis. A kit conforming to the present invention includes reagents capable of measuring the expression of specific proteins in skin cells and/or skin tissues, wherein the specific proteins change their expression with inflammation caused by atopic dermatitis.

In an example, a kit conforming to the present invention includes as reagents antibodies capable of specifically recognizing specific proteins whose expression changes with inflammation caused by atopic dermatitis.

The specific proteins should ideally be selected from a group consisting of Apolipoprotein A1, FABP-4, FABP-5, Vimentin, Rho GDI, Annexin II, Enolase 1, Galectin-1, Galectin-3, Galectin-4, Galectin-7, Galectin-8, PARK7, Desmin, Moesin, Ezrin, Radixin, HSP70, HSP90, Serum albumin, Immunoglobulin G, Arginase I and Uracil-DNA glycosylase.

The kit may also include a tape for collecting skin tissues, a set of reagents for immunochemically detecting the proteins collected on the tape, and an operating manual, among others. Ideally the operating manual should describe, among others, how to use the kit, as well as the judgment criteria for determining atopic dermatitis.

In another example, a kit conforming to the present invention includes as reagents nucleic acid probes capable of specifically hybridizing with mRNA of specific proteins whose expression changes with inflammation caused by atopic dermatitis.

The specific proteins should ideally be selected from a group consisting of Apolipoprotein A1, FABP-4, FABP-5, Vimentin, Rho GDI, Annexin II, Enolase 1, Galectin-1, Galectin-3, Galectin-4, Galectin-7, Galectin-8, PARK7, Desmin, Moesin, Ezrin, Radixin, HSP70, HSP90, Serum albumin, Immunoglobulin G, Arginase I and Uracil-DNA glycosylase.

The kit may also include a tape for collecting skin tissues, reagents for extracting RNA from the skin tissues collected on the tape, reagents for analyzing RNA using the Northern blotting method, and an operating manual, among others. Ideally the operating manual should describe, among others, how to use the kit, as well as the judgment criteria for determining atopic dermatitis.

In yet another example, a kit conforming to the present invention includes as reagents a pair of nucleic acid primers including a nucleic acid primer capable of specifically hybridizing with mRNA of specific proteins whose expression changes with inflammation caused by atopic dermatitis, and a nucleic acid primer capable of specifically hybridizing with cDNA synthesized using the aforementioned mRNA as a mold.

The specific proteins should ideally be selected from a group consisting of Apolipoprotein A1, FABP-4, FABP-5, Vimentin, Rho GDI, Annexin II, Enolase 1, Galectin-1, Galectin-3, Galectin-4, Galectin-7, Galectin-8, PARK7, Desmin, Moesin, Ezrin, Radixin, HSP70, HSP90, Serum albumin, Immunoglobulin G, Arginase I and Uracil-DNA glycosylase.

The kit may also include a tape for collecting skin tissues, reagents for extracting RNA from the skin tissues collected on the tape, reagents for analyzing RNA using the RT-PCR method, and an operating manual, among others. Ideally the operating manual should describe, among others, how to use the kit, as well as the judgment criteria for determining atopic dermatitis.

The present invention also provides a method for identifying substances effective in the treatment and/or prevention of atopic dermatitis. This method includes the following steps:
(a) a step to cause a target substance to contact skin cells and/or skin tissues;
(b) a step to culture for a specified time the skin cells and/or skin tissues contacted by the target substance in step (a);
(c) a step to measure the expression of specific proteins and/or their genes in the skin cells and/or skin tissues cultured in step (b), wherein the specific proteins change their expression with inflammation caused by atopic dermatitis; and
(d) a step to evaluate the effects of the target substance on the expression of the specific proteins and/or their genes in skin cells and/or skin tissues, by comparing the expression of the specific proteins and/or their genes measured in step (c) against the expression of the specific proteins and/or their genes in control skin cells and/or skin tissues.

The target substance may be any substance, such as a protein, peptide, vitamin, hormone, polysaccharide, oligosaccharide, monosaccharide, low-molecular compound, nucleic acid (DNA, RNA, oligonucleotide, mononucleotide, etc.), lipid, other natural compound, synthetic compound, plant extract, fraction of plant extract, or any mixture thereof.

Skin cells and skin tissues are as described above.

The target substance may be caused to contact skin cells and/or skin tissues using any method. Examples include a method to add the target substance in a culture solution of skin cells and/or skin tissues, and a method to culture skin cells and/or skin tissues in a culture container or on a culture sheet on which the target substance has been applied or fixed. It is also possible to use a method to apply the target substance directly over the skin, or orally administer the target substance, using a life form such as human or other mammal (such as mouse, rat, guinea pig, rabbit, pig, etc.).

The culture time of skin cells and/or skin tissues is not specifically limited, and a desired time can be set as long as it is enough to check whether the target substance has any effect on the expression of specific proteins or their genes in skin cells and/or skin tissues.

If normal human epidermal keratinocytes are used as skin cells, for example, a culture time of 12 to 48 hours is appropriate, and that of 12 to 24 hours is preferable. Here, "culture skin cells and/or skin tissues" means growing/proliferating skin cells and/or skin tissues, and the definition also encompasses sustaining the life of, breeding and rearing life forms having skin cells or skin tissues in addition to growing/proliferating isolated single skin cells and/or skin tissues.

The control skin cells and/or skin tissues to be compared against may be skin cells and/or skin tissues not yet contacted by the target substance. They may also be skin cells and/or skin tissues that have been given the same treatment except that they do not contact the target substance.

The specific proteins should ideally be selected from a group consisting of Apolipoprotein A1, FABP-4, FABP-5, Vimentin, Rho GDI, Annexin II, Enolase 1, Galectin-1, Galectin-3, Galectin-4, Galectin-7, Galectin-8, PARK7, Desmin, Moesin, Ezrin, Radixin, HSP70, HSP90, Serum albumin, Immunoglobulin G, Arginase I and Uracil-DNA glycosylase.

In an example of the present invention, the amount of expression of Apolipoprotein A1, FABP-5, Vimentin, Rho GDI, Annexin II, Enolase 1, Serum albumin or Immunoglubulin G in skin cells and/or skin tissues contacted by the target substance is compared against the control and if the former decreases, and the target substance is determined to have the effect of decreasing the expression of this protein, the target substance can be identified as effective in the treatment and/or prevention of atopic dermatitis.

In another example of the present invention, the amount of expression of FABP-4, Galectin-1, Galectin-3, Galectin-4, Galectin-7, Galectin-8, PARK7, Desmin, Moesin, Ezrin, Radixin, HSP70, HSP90, Arginase I or Uracil DNA glycosylase in skin cells and/or skin tissues contacted by the target substance is compared against the control and if the former increases, and the target substance is determined to have the effect of increasing the expression of this protein, the target substance can be identified as effective in the treatment and/or prevention of atopic dermatitis.

EXAMPLES

The present invention is explained below in details using examples. It should be noted, however, that the present invention is not at all limited to these examples.

Example 1

Materials and Method of Experiment
1. Haptene Treatment of Mice (NC/Nga mice) Modeling Atopic Dermatitis Six-week-old male mice (NC/Nga mice) modeling atopic dermatitis were obtained (NC/Nga slc, Sankyo Labo Service Corporation) and raised under conventional conditions. NC/Nga mice have different pedigrees and the ones used in this study came from the pedigree of NC/Nga mice that do not develop atopic dermatitis only through raising in a conventional environment and will develop atopic dermatitis only when an immune inducer such as DNFB (Dinitorofluorobenzene) is administered. In view of the above, a 0.1% DNFB solution (haptene) was applied to the skin of the mice on both ears as well as the right and left sides of the back once a week for a total of 4 weeks.

To relieve inflammation caused by atopic dermatitis, lactoferrin was dissolved in drinking water at 1 µg/ml and administered.

Three mice were tested under each of the following experimental conditions: (1) haptene (−)/lactoferrin (−), (2) haptene (−)/lactoferrin (+), (3) haptene (+)/lactoferrin (−), and (4) haptene (+)/lactoferrin (+).

2. Extraction of Protein from Skin Tissues of Mice Modeling Atopic Dermatitis

Skin tissues were cut out from mice treated with haptene/lactoferrin for 4 weeks and the tissue strips were cut into small pieces with a knife, after which the tissue pieces were transferred into a centrifugal tube whose tare weight had been measured beforehand, to measure the tissue weight. Different buffers were added by different amounts, such as tissue weight×0.85 mg Urea, tissue weight×0.1 µl 1.5% SDS, tissue weight×0.1 µl 8.5% Triton X-100, and tissue weight×0.05 µl 2-ME, and homogenized using a HG30 homogenizer (Hitachi, Ltd.). After centrifuging the samples for 30 minutes at 15,000 rpm (15,000×g) and 10° C., the supernatant was collected and this supernatant was again centrifuged for 1 hour at 50,000 rpm (100,000×g) and 10° C., after which the obtained supernatant was used as a sample. Protein content was quantified using the dot blotting method.

3. Extraction of Protein from Skin Tissues of Atopic Dermatitis Patients

Pieces of a horny cell layer checker (Asahi Biomed Co., Ltd.) were attached to inflammatory areas (mainly arms) and nearby non-inflammatory areas of atopic dermatitis patients to collect horny cell layer samples. Control samples were also collected from subjects not suffering from atopic dermatitis. Three pieces of the horny cell layer checker were attached to each location and then collected. Using 50 µl of a 1× sample buffer (83 mM Tris-HCl (pH 6.8), 2.7% SDS, 28% glycerin) per seal, samples were scraped off from the seal using a scraper. The collected sample was centrifuged for 10 minutes at 15,000 rpm (15,000×g) and 4° C., after which the supernatant was collected and proteins were quantified using a DC protein assay (Bio-Rad Laboratories Inc.).

4. Two-Dimensional Gel Electrophoresis (2-DE)

4-1 First-Dimension Isoelectric Focusing Electrophoresis

60 µg of protein was mixed in a gel-swelling solution (5M urea, 2M thiourea, 0.5% ampholytes (pH 3.5 to 10) (Amersham Biosciences, Inc.), 0.0025% Orange G, 2.5 mM TBP, 1% Triton X-100) until the total quantity became 340 µl, after which the mixture was let swell overnight in a Immobiline DryStrip gel (18 cm, pH 3 to 10, NL) (Amersham Biosciences, Inc.) at 20° C. Using a device by Anatech Co., Ltd., in the first dimension isoelectric focusing electrophoresis was then performed using a program specifying 500 V for 2 hours, 700 V for 1 hour, 1000 V for 1 hour, 1500 V for 1 hour, 2000 V for 1 hour, 3000 V for 1 hour, and 3500 V for 10 hours at 20° C. After the electrophoresis, the gel was equalized for 1 hour at room temperature using a SDS equalization buffer (5.8M urea, 0.06M thiourea, 0.5% dithiothereitol (DTT) (w/v), 25% glycerol, 0.0025% BPB).

4-2 Second-Dimension SDS-PAGE

In the second dimension, SDS-PAGE was performed using a Tris-Tricine buffer (cathode buffer: 0.05M Tris, 0.05M tricine, 0.05% SDS; anode buffer: 1M Tris-HCl (pH 8.8)) and 7.5% acrylamide gel of 18 cm×18 cm.

4-3 Electrophoresis Blotting Method

The gel completing SDS-PAGE was transferred for 2 hours to PVDF membranes of 20 cm×20 cm (ProBlott Membranes (Applied Biosystems, Inc.)) using a semi-dry type transfer system (Nihon Eido Co., Ltd.) at a constant current of 150 mA. For the transfer buffer, anode liquid 1 comprising 0.3M Tris-HCl (pH 10.4) and 20% methanol, anode liquid 2 comprising 25 mM Tris-HCl (pH 10.4) and 20% methanol, and cathode liquid comprising 25 mM Tris-HCl (pH 10.4), 20% methanol and 40 mM 6-amino hexanoic acid (Wako Pure Chemical Industries, Ltd.) were used. The transferred gel was washed three times for 20 minutes each using a TTBS buffer (20 mM Tris-HCl (pH 7.5) (Bio-Rad Laboratories Inc.), 500 mM NaCl, 0.3% Tween 20 (Bio-Rad Laboratories Inc.)), and then further washed three times for 2 minutes each using MQW. Next, the membranes were sealed and soaked in 50 ml of a gold colloidal solution (Colloidal Gold Total Protein Stain (Bio-Rad Laboratories Inc.)), and the solution was shaken for 1 to 2 hours to stain the protein. Once the membranes had been stained, the gold colloidal solution was removed and the residue was washed five times for 1 minute each using pure water and then dried.

5. Identification of Protein 5-1 Reduced S-Alkylation and Protease Digestion of Protein Transferred to PVDF Membranes Spots were cut off from the protein transferred to PVDF membranes and placed in a tube, to which 100 to 300 μl of a reducing buffer (8M guanidine-HCl (pH 8.5), 0.5M Trisbase, 0.3% EDTA-2Na (w/v), 5% acetonitrile) was added. Next, around 1 mg of DTT (dithiothreitol) dissolved in reducing buffer was added to replace the interior of the tube with nitrogen gas, after which the tube was left stationary at room temperature for 1 hour to reduce the protein. Before the reaction was completed, around 3 mg of a monoiodoacetic acid dissolved in 1M NaCl was added and the mixture was agitated continuously for 15 to 20 minutes by blocking light to achieve S-carboxymethylation. Thereafter, the PVDF membranes were removed and washed for 5 minutes using pure water under agitation, after which the membranes were agitated in a similar manner in 2% acetonitrile. The PVDF membranes were then removed and transferred into a tube containing a Lys-C digesting buffer (70% acetonitrile/20 mM Tris-HCl (pH 9.0)) and rinsed two to three times, followed by a complete submersion in the Lys-C digesting buffer to implement protease digestion for 1 hour.

5-2 Mass Spectrometry and Peptide Mass Finger Printing

The protease-digested solution was diluted seven times to an acetonitrile concentration of 10%. As a pretreatment, suction and discharge was repeated several times using 50% acetonitrile/0.1% TFA (trifluoro-acetic acid), and several times using 2% acetonitrile/0.1% TFA (trifluoro-acetic acid), in order to activate the filler part of the ZipTipc18 pipette tip (Millipore Corporation). Next, a protease-digested solution was suctioned and discharged several times using the activated ZipTipc18 pipette tip to cause the fragmented peptide to be adsorbed to the filler part. Furthermore, 2% acetonitrile/0.1% TFA (trifluoro-acetic acid) was suctioned and discharged several times to remove salts. Next, 0.5 to 1 μl of a saturated matrix solution dissolved in 50% acetonitrile/0.1% TFA (trifluoro-acetic acid) was suctioned, and after approx. 10 seconds the suctioned solution was dripped onto the target probe supplied with the mass spectrometer. The sample was dried and solidified, and then measured with the mass spectrometer (MALDI-TOF MS). Based on the obtained value of mass, the protein was identified using a database (MS-Fit, Mascot Search).

6. Western Blotting Method

SDS-PAGE was performed with a Laemmli Tris-Glycin system using a Western blotting sample. After the SDS-PAGE, a gel was transferred to PVDF membranes (Millipore Corporation) at a constant current of 0.8 mA per 1 $cm^2$, and then soaked in 5% skim milk/PBS (−) and blocked overnight at 4° C. The membranes were washed three times using 0.1% Tween 20/PBS (−), and then reacted with the primary antibody for 1 hour at room temperature. The sample was then shaken for 1 hour with a secondary antibody where, if Biotinylated anti-goat IgG (Vector Laboratories, Inc.) (1:1000 dilution) was used as the secondary antibody, Alkaline phosphatase-conjugated avidin D (Vector Laboratories, Inc.) (1:1000 dilution) was reacted for 1 hour and then 0.6 mg/ml 5-bromo-4-chloro-3-indolylphosphate, 1.2 mg/ml nitrobluetetrazolium, 0.1M Tris-HCl (pH 9.5) and 5 mM $MgCl_2$ were used to develop color. If HRP labeled anti-mouse IgG (Amersham Bioscience, Inc.) (1:1000 dilution), HRP labeled anti-rabbit IgG (Amersham Bioscience, Inc.) (1:1000 dilution), HRP labeled anti-rat IgG (Amersham Bioscience, Inc.) (1:1000 dilution) or HRP labeled anti-goat IgG (Santa Cruz Biotechnology, Inc.) (1:1000 dilution) was used as the secondary antibody, an enhanced chemiluminescence (ECL) kit (Amersham Bioscience, Inc.) was used to implement detection by means of fluorescence color development. The types of primary antibodies used, and their dilution factors, are as follows: Mouse anti-HSP70 monoclonal antibody (Santa Cruz Biotechnology, Inc.) (1:1000 dilution), rabbit anti-annexin II polyclonal antibody (Santa Cruz Biotechnology, Inc.) (1:1000 dilution), mouse anti-HSP90 monoclonal antibody (Santa Cruz Biotechnology, Inc.) (1:1000 dilution), rat anti-GRP94 monoclonal antibody (StressGen, Inc.) (1:1000 dilution), mouse anti-galectin-1 monoclonal antibody (R&D Systems, Inc.) (1:1000 dilution), rat anti-galectin-3 monoclonal antibody (R&D Systems, Inc.) (1:1000 dilution), mouse anti-galectin-4 monoclonal antibody (R&D Systems, Inc.) (1:1000 dilution), mouse anti-galectin-7 monoclonal antibody (R&D Systems, Inc.) (1:1000 dilution), mouse anti-galectin-8 monoclonal antibody (R&D Systems, Inc.) (1:1000 dilution), goat anti-galectin-9 polyclonal antibody (Santa Cruz Biotechnology, Inc.) (1:1000 dilution), rabbit anti-desmin polyclonal antibody (Santa Cruz Biotechnology, Inc.) (1:1000 dilution), goat anti-vimentin polyclonal antibody (Santa Cruz Biotechnology, Inc.) (1:1000 dilution), rabbit anti-enolase-1 polyclonal antibody (Santa Cruz Biotechnology, Inc.) (1:1000 dilution), rabbit anti-ezrin/radixin/moesin polyclonal antibody (Chemicon, Inc.) (1:1000 dilution), goat anti-FABP-4 polyclonal antibody (G-T Research, Inc.) (1:1000 dilution), mouse anti-apolipoprotein A1 monoclonal antibody (ICN Biomedicals, Inc.) (1:1000 dilution), goat anti-apolipoprotein A1 (Abcom, Inc.) (1:1000 dilution), goat anti-PARK7 polyclonal antibody (Abcom, Inc.) (1:1000 dilution), mouse anti-Rho GDI monoclonal antibody (Santa Cruz Biotechnology, Inc.) (1:1000 dilution), goat anti-FABP-5 polyclonal antibody (R&D Systems, Inc.) (1:1000 dilution), mouse anti-SCCA2 monoclonal antibody (Santa Cruz Biotechnology, Inc.) (1:1000 dilution), rabbit anti-FABP-5 polyclonal antibody (BioVendor, Inc.) (1:5000 dilution), and rabbit anti-human albumin polyclonal antibody (Intercell AG) (1:1000 dilution).

7. Measurement of Degree of Decrease in Keratinocyte Area

A horny cell layer checker was pressed against the affected part to separate keratinocytes. The horny cell layer checker onto which keratinocytes had been collected was then stained with an aqueous solution of 1% brilliant green and 0.5% gentian violet and then observed using a digital microscope (VHX-100, Keyence Co., Ltd., Japan) (the method employed by Kashibuchi et al. was modified; JSCCJ, 23, 1, 1989). The obtained images were visually evaluated for keratinocyte area by expert judges to give a score over five levels (1: small, 2: slightly small, 3: average, 4: slightly large, 5: large).

8. Measurement of Transepidermal Water Loss

Measurement was performed using a commercial device called Tewameter (TEWAMETER TM210, Courage+Khazaka electronic GmbH). The measurement principle is that, by assuming that water diffuses from skin surface into air according to Fick's law, vapor pressures were obtained at two several-millimeter points on the skin to calculate the amount of water evaporating from the epidermis.

9. Measurement of Marker Protein Using ELISA (Enzyme-Linked Immunosorbent Assay)

A keratinocyte protein solution, which had been diluted to 0.2 μl/μl with a phosphoric acid buffer solution (PBS), was added to a 96-well ELISA plate at 50 μl per well to cause adsorption for 18 hours at 4° C. After removing the keratinocyte protein solution, the plate was soaked in a blocking solution (PBS containing 1% bovine serum albumin (BSA)) to cause blocking for 1 hour at 37° C. The plate was then washed with a washing solution (PBS containing 0.05% polyoxyethylene (20) sorbitan monolaurate (Wako Pure Chemical Industries, Ltd.)), after which a primary antibody solution (each of various antibodies prepared to 5 mg/ml using a washing solution) was added at 50 µl per well to cause reaction for 2 hours at 37° C.

The obtained plate was washed and then a secondary antibody solution (anti-mouse HRP (Horseradish peroxidase) immunoglobulin G (Vector Laboratories, Inc.) prepared to 1 mg/ml using a washing solution, or anti-rabbit HRP (Horseradish peroxidase) immunoglobulin G (Vector Laboratories, Inc.) prepared to 1 mg/ml using a washing solution) was added by 50 µl per well to cause reaction for 1 hour at 37° C. The obtained plate was again washed, and then an enhanced chemiluminescence (ECL) kit (Amersham Bioscience, Inc.) was used to cause chemiluminescent reaction, and values were detected using a chemiluminescent detector (SpectraMax Lmax II 384 by Molecular Devices Corp.).

Result of Experiment

1. Haptene Treatment of Mice Modeling Atopic Dermatitis

When raised with haptene treatment in a conventional environment, the mice (NC/Nga mice) modeling atopic dermatitis used in this study developed a macroscopically noticeable dermatitis very similar to atopic dermatitis after 4 weeks of haptene treatment. In this study, the mice were fed with drinking water mixed with lactoferrin, a substance shown to be effective on atopic dermatitis (a protein with a molecular weight of 80,000 found in saliva and blood and bonding with Fe ions). When the mice thus raised with haptene and lactoferrin were observed, the mice on which haptene was applied developed an inflammation very similar to human atopic dermatitis on their back, while the mice on which haptene was applied and to which water mixed with lactoferrin was also given developed less inflammation compared to the haptene-treated mice not given lactoferrin (FIG. 1). This suggests that, if a protein whose expression had changed due to development of atopy as a result of haptene treatment has returned to the same level as its expression in the mice not given any treatment because of the effect of lactoferrin treatment to relieve atopic condition, the protein is then considered a promising marker.

2. Analysis by Two-Dimensional Electrophoresis of Skin Tissues from Mice Modeling Atopic Dermatitis To identify proteins involved in atopic dermatitis, skin samples collected from the mice on which haptene was/was not applied and to which lactoferrin was/was not given were analyzed by two-dimensional electrophoresis to analyze changing proteins.

Skin samples were taken from the mice not given any treatment (control), mice on which haptene was applied, control mice given lactoferrin, and mice on which haptene was applied and to which lactoferrin was also given (samples were taken from inflammatory area in the case of haptene-treated mice), and each sample was mixed with a sample buffer according to the weight and then crushed using a Polytron homogenizer, after which the sample was centrifuged for 30 minutes at 15,000 rpm (15,000×g) to collect the supernatant. This supernatant was ultra-centrifuged for 1 hour at 100,000×g and the obtained supernatant was used as a sample. Two-dimensional electrophoresis was performed using a strip gel of pH 3 to 10 in the first dimension, and using a 7.5% acrylic amide gel in the second dimension. Gold colloidal staining was used to detect changing proteins and those proteins that had changed were identified using a mass spectrometer (MALDI-TOF MS) (FIG. 2A, 2B). As a result, 43 of the 49 proteins analyzed were identified as having undergone change. Of the identified proteins, those whose expression increased in the haptene-treated mice (mice suffering from inflammation caused by atopic dermatitis) include FABP-5, Apolipoprotein A1 and Vimentin, but there were also four unknown proteins. On the other hand, Galectin-3, Desmin and PARK7 were identified, among others, as proteins whose expression decreased in the haptene-treated mice. Many of the identified proteins were cytoskeletal proteins such as Keratin 5, Keratin 16, Desmin, Vimentin and Moesin.

3. Antibody Confirmation of Changing Proteins Using Mice Modeling Atopic Dermatitis To confirm that the expression of the above proteins changes with development of atopic dermatitis, various antibodies were used to conduct Western blotting analysis. First, the Galectin family was given attention because Galectin-3 was included in the proteins identified from the result of two-dimensional electrophoresis. Galectins are a type of glycoprotein and do not have a normal signal sequence, but they are released to outside the cell when a stimulation is received due to immune response, etc., or sometimes without any stimulation. Each Galectin molecule exhibits a different tissue distribution, and involvement of Galectin molecules in different physiological phenomena such as immune control, cell/matrix bonding, cell/cell bonding and healing of wounds has been reported (refer to J. Biol. Chem. 264: 1310-1316 (1989), J. Biochem. 104: 1-4 (1988), Proc. Natl. Acad. Sci. USA. 87: 7324-7328 (1990), Eur. J. Biochem. 248: 225-230 (1997), Dev. Biol. 168: 259-271 (1995), J. Biol. Chem. 270: 5823-5829 (1995), and Proc. Natl. Acad. Sci. USA. 93: 7252-7257 (1996)).

In light of the above, antibodies of Galectin-1, -3, -4, -7, -8 and -9 were used to examine how the amounts of expression of these other members of the Galectin family, besides Galectin-3, would change in the skin of mice modeling atopic dermatitis (FIG. 3). As a result, the amounts of expression of Galectin-1, -3, -4, -7 and -8 decreased in the haptene-treated mice compared to the non-treated mice (control mice). On the other hand, the amounts of expression of Galectin-1, -4, -7 and -8 recovered in the haptene-treated mice also given lactoferrin, to levels close to the non-haptene-treated mice (control mice). Galectin-9 is deemed to have little association with atopic dermatitis because it did not show any change as a result of haptene treatment.

Desmin, Moesin/Ezrin/Radixin and Vimentin, all of which are cytoskeletal proteins, were analyzed in a similar manner (FIG. 4). In the haptene-treated mice, the amount of expression of Desmin decreased compared to the non-treated control mice, but the amounts of expression of Moesin/Ezrin/Radixin (50-kDa, severed type) and Vimentin increased. Particularly with Moesin, Ezrin and Radixin, severed types of low molecular weight increased significantly due to haptene treatment, but they did not decrease as a result of lactoferrin administration. For your information, Moesin, Ezrin and Radixin are proteins belonging to the same family and Moesin was identified by two-dimensional electrophoresis. Since the antibodies used in this study have the capability to recognize these three types of protein, higher levels of expression of Moesin or other protein or a combination of Moesin and other protein or proteins may have been detected due to inflammation.

As for HSP70, HSP90 and GRP94, all of which are heat shock proteins, the amounts of expression of HSP70 and HSP90 decreased in the haptene-treated mice compared to the non-treated mice (control mice), but the expression of GRP94 did not change regardless of whether or not haptene treatment was given (FIG. 4).

Furthermore, FABP-4 (Fatty acid binding protein-4), FABP-5 (Fatty acid binding protein-5), Enolase 1, PARK7

(DJ-1), Annexin II, Apolipoprotein A1 and Rho GDI were analyzed using the Western blotting method (FIG. 5). As a result, the amounts of expression of Annexin II, Enolase 1, FABP-4 and PARK7 decreased in the haptene-treated mice compared to the non-treated mice (control mice). With all of the above proteins other than FABP-4, the amount of expression recovered in the haptene-treated mice also given lactoferrin, to a level close to the non-haptene-treated mice (control mice). On the other hand, the amounts of expression of Rho GDI, FABP-5 and Apolipoprotein A1 increased in the haptene-treated mice compared to the non-treated mice (control mice) (FIG. 5). Rho GDI is known to weaken intercellular bonds, and an increase in this protein due to development of atopy may be related to the detachment of skin due to atopic dermatitis.

4. SDS-PAGE Analysis Using Skin Tissues from Atopic Dermatitis Patients

Based on the above results, candidate atopic dermatitis markers could be narrowed down using the mice modeling atopic dermatitis. However, these proteins had to be examined further to see if they could be used as markers for human atopic dermatitis. Accordingly, a seal-type device called a horny cell layer checker was used to collect samples from inflammatory areas (A.P. in FIG. 6) and non-inflammatory areas (control) of subjects suffering from atopic dermatitis, and also from corresponding areas (control) of volunteer subjects not suffering from atopic dermatitis. Samples were collected by applying three seals to each location of human skin, and a 1×SDS sample buffer was used to dissolve the collected human tissues. Thereafter, the samples from atopic patients (2) and healthy subjects (3) were examined by SDS-PAGE to identify, using a mass spectrometer (MALDI TOF-MS), those proteins whose expression increased in the samples collected from the atopic patients. The result found that Annexin II, Squamous cell carcinoma antigen 1 (SCCA1), Squamous cell carcinoma antigen 2 (SCCA2), Fatty acid binding protein-5 (FABP-5), Serum albumin and Immunoglobulin G increased their expression with development of atopy (FIG. 6). On the other hand, Arginase I and Uracil-DNA glycosylase were found to decrease in their expression in the atopic patients (FIG. 6).

5. Analysis Using Various Antibodies of Skin Tissues From Atopic Dermatitis Patients The Western blotting analysis using mice modeling atopic dermatitis caused changes in 17 proteins. Accordingly, these proteins were studied to see if they would also exhibit similar changes in humans due to inflammation caused by human atopic dermatitis (FIG. 7). At the same time, the proteins exhibiting change in the SDS-PAGE analysis using skin tissues of atopic dermatitis patients were also examined.

Annexin II increased its expression in the affected areas (A.P. in FIG. 7) of atopic dermatitis patients compared to non-affected areas (control) and when compared to the bands of healthy subjects, the molecular weight was also slightly smaller. Although the reason for this molecular difference is not clear, it may be related to the different physical constitutions of atopic dermatitis patients and healthy subjects.

Enolase 1 and Squamous cell carcinoma antigen 2 (SCCA2) increased their expression in the affected areas of one atopic dermatitis patient.

As for PARK7, although its expression both increased and decreased in different atopic dermatitis patients, there was a general trend of decrease in expression among the atopic dermatitis patients compared to healthy subjects.

As for Apolipoprotein A1, there was no expression at all in the healthy subjects and in the non-affected areas of atopic dermatitis patients, and the expression of this protein increased only in the affected areas of atopic dermatitis patients.

The above results are summarized in Table 1.

TABLE 1

| <Expression increased with inflammation caused by atopic dermatitis> | | <Expression decreased with inflammation caused by atopic dermatitis> | |
|---|---|---|---|
| Atopy-modeling mice | | | |
| Apolipoprotein A1 | +++ | Galectin-1, -3, -7 | +++ |
| FABP-5 | ++ | PARK 7 | ++ |
| Vimentin | ++ | Desmin | ++ |
| Rho GDI | ++ | Annexin II | ++ |
| | | FABP-4 | ++ |
| Human skin tissues suffering from atopy | | | |
| Apolipoprotein A1 | +++ | PARK 7 Note 3) | ++ |
| FABP-5 | ++ | | |
| SCCA2 Note 2) | ++ | | |
| Annexin II Note 2) | ++ | | |
| Enolase-1 Note 2) | ++ | | |

Note 1)
The number of + marks indicates the level of expression as measured by the Western blotting method.
Note 2)
Expression varied in different atopic patients.
Note 3)
Expression also decreased in non-inflammatory areas of atopic patients. Whether the change was increase or decrease varied in inflammatory areas of patients.

6. Analysis Using Various Antibodies of Human Tissues from Patients

To confirm the practical utility of candidate atopic dermatitis markers detected in the skin tissues of mice modeling atopic dermatitis as well as a small number of atopic dermatitis patients, skin samples collected from 17 volunteer patients suffering from atopic dermatitis based on a diagnosis by a dermatologist (7 males, 10 females), and 15 healthy volunteers (10 males, 5 females), were used to study the correlation with the severity of atopic dermatitis. Based on the classification of severity of atopic dermatitis in patients (Revised Guidelines for Therapy for Atopic Dermatitis 2004, by the Japanese Dermatological Association), 1 patient had severity level 1 atopic dermatitis, 2 patients had severity level 2 atopic dermatitis, 6 patients had severity level 3 atopic dermatitis, and 3 patients had severity level 4 atopic dermatitis. Data of eosinophils, IgE and LDH in blood stream, which are already known to have a correlation with the severity of atopic dermatitis, was also collected from the 17 volunteer atopic dermatitis patients. Skin samples were collected using a horny cell layer checker and the expression of six proteins was analyzed using the Western blotting method (FIGS. 8A, 8B).

Enolase 1 was not detected in the skin of healthy subjects, but it expressed widely in the skin of atopic dermatitis patients. Twelve out of 17 patients showed more expression of Enolase 1 in inflammatory areas than in non-inflammatory areas. Two patients showed decreased levels of Enolase 1 expression.

Fatty acid binding protein-5 (FABP-5) was virtually undetectable in the skin of healthy subjects except for 1 subject, but it expressed strongly in the inflammatory areas of atopic dermatitis patients according to the severity of condition. Thirteen out of 17 patients showed more expression of FABP-5 in inflammatory areas than in non-inflammatory areas.

Squamous cell carcinoma antigen 2 (SCCA2) clearly increased their expression in the skin of atopic dermatitis patients, although 1 healthy subject also exhibited a weak expression of the protein. Nine out of 17 patients showed more expression of SCCA2 in inflammatory areas than in non-inflammatory areas. There was 1 patient in whom the protein decreased in its expression. The expression of SCCA2 was more uneven compared to FABP-5.

As for Apolipoprotein A1, there was a weak expression in the skin of 1 healthy subject, while the protein was detected strongly in specific atopic dermatitis patients. Nine out of 17 patients showed more expression of Apolipoprotein A1 in inflammatory areas than in non-inflammatory areas, and the expression decreased in 1 patient.

Serum albumin was detected relatively strongly in all atopic dermatitis patients, and the differences between inflammatory and non-inflammatory areas were small in general. Healthy subjects showed only a weak expression of this protein, except for 1 subject.

Annexin II was detected widely, although at a weak level, in the skin of atopic dermatitis patients, while the protein was virtually undetectable in healthy subjects. Six out of 17 patients showed more expression of Annexin II in inflammatory areas than in non-inflammatory areas, and the expression of this protein decreased in 6 patients.

By excluding Annexin II associated with a low level of expression intensity, samples for the five marker proteins of Enolase 1, FABP-5, SCCA2, Apolipoprotein A1 and Serumalbumin were examined to quantify their expression intensity. The results are summarized by severity of patient's condition in FIGS. 9A, 9B.

Since FABP-5, Serum albumin and Enolase 1 showed high correlation with the severity of patient's skin condition, these proteins can be used to determine the severity of atopic dermatitis affecting each patient. Serum albumin was also detected in non-inflammatory areas, indicating that its expression is reflective of the physical constitution of the patient suffering from atopic dermatitis. Apolipoprotein A1 and SCCA2 showed uneven expression levels, while Annexin II showed high levels of expression in non-inflammatory areas. The expression of each of these markers may also be reflective of the physical constitution of the patient. The above results are summarized in Table 2.

TABLE 2

| <Expression decreased with inflammation caused by atopic dermatitis> | | |
|---|---|---|
| <Expression increased with inflammation caused by atopic dermatitis> | | <Expression decreased with inflammation caused by atopic dermatitis> |
| Human skin tissues suffering from atopy | | |
| Apolipoprotein A1 | ++ | Not applicable |
| FABP-5 | ++ | |
| SCCA2 | ++ | |
| Annexin II | ++ | |
| Enolase-1 | ++ | |
| Albumin | +++ | |
| Galectin-7 | +++ | |

Note)
The number of + marks indicates the level of expression as measured by the Western blotting method.

7. Utility Verification of Markers in Patients with a History of Atopic Dermatitis Around 6.34 million people have visited a hospital at least once due to atopic dermatitis, and the number of people having allergic skin reactions and suffering from conditions of atopic dermatitis is estimated to be around 12 million. In addition to drug treatment, skin care treatment using moisture-keeping agents is also shown to be effective on atopic dermatitis (Hachiro Tagami, Fragrance Journal, p. 13-19, June 2003) and many of those suffering from atopic dermatitis are resorting to a skin care regimen using quasi-drugs and cosmetics. Based on the above, the markers identified in this study may be applicable, in addition to diagnosis of atopic dermatitis by dermatologists, in skin diagnosis conducted by beauty counselors or by users themselves at home. Accordingly, subjects who had suffered atopic dermatitis before and received treatment by a dermatologist were examined to confirm the practical utility of the candidate atopic dermatitis markers.

Some of the known characteristic changes caused by atopic dermatitis include increase in transepidermal water loss (TEWL) due to a weakened barrier function of the skin's horny cell layer, decrease in keratinocyte area due to dyskeratosis, and presence of nucleated cells in the horny cell layer (Tagami H. et al., J. Invest. Dermatol. Symp. Proc., 6, 1, 87-94, 2001). Accordingly, the level of increase in TEWL and level of decrease in keratinocyte area were used as inflammation level indicators for atopic dermatitis to verify the utility of the candidate markers.

A group of volunteers including 11 healthy subjects and 10 subjects with a history of atopic dermatitis were evaluated. Samples from normal areas on the inside of the upper arm were collected from healthy subjects and subjects with a history of atopic dermatitis, while samples were also collected from inflammatory areas of subjects with a history of atopic dermatitis (inside the elbow on 7 patients, neck on 1 patient, between fingers on 1 patient, and back of the knee on 1 patient), and the collected samples were used to examine the correlations between the increase in TEWL/decrease in keratinocyte area on one hand, and the degrees of expression of six candidate markers (FABP-5, Galectin-7, Enolase 1, SCCA2, Apolipoprotein A1 and Annexin II) on the other. Decrease in keratinocyte area was measured using the separated-horny-cell-layer staining method, while increase in TEWL was measured using a Tewameter. Degree of expression was measured for the six candidate markers using the ELISA method by extracting each protein from samples of horny cell layer collected with a horny cell layer checker from normal areas on the inside of the upper arm of healthy subjects and subjects with a history of atopic dermatitis, and also from inflammatory areas of subjects with a history of atopic dermatitis.

FIG. 10 shows the resulting correlations between the increase in TEWL and the levels of expression of six candidate markers (FABP-5, Galectin-7, Enolase 1, SCCA2, Apolipoprotein A1 and Annexin II). Although TEWL, shown by the X-axis in the graphs provided in FIG. 10, was virtually the same in normal areas of healthy subjects and subjects with a history of atopic dermatitis, it increased in inflammatory areas of subjects with a history of atopic dermatitis. The expressions of three markers including FABP-5, Galectin-7 and Enolase 1, shown by the Y-axis in the graphs provided in FIGS. 10A to 10C, increased more in proportion to the increase in TEWL in inflammatory areas of subjects with a history of atopic dermatitis, compared to normal areas of healthy subjects and subjects with a history of atopic dermatitis. On the other hand, the levels of expression of the remaining three markers including SCCA2, Apolipoprotein A1 and Annexin II, shown by the Y-axis in the graphs provided in FIGS. 10D to 10F, followed the order of "Healthy subjects<Normal areas of subjects with a history of atopic dermatitis<Inflammatory areas of subjects with a history of atopic dermatitis," suggesting that these markers are useful in the diagnosis of risk of developing atopic dermatitis.

FIG. 11 shows the resulting correlations between the level of decrease in keratinocyte area and the levels of expression of six candidate markers (FABP-5, Galectin-7, Enolase 1, SCCA2, Apolipoprotein A1 and Annexin II). Although keratinocyte area, shown by the X-axis in the graphs provided in FIG. 11, was virtually the same in normal areas of healthy subjects and subjects with a history of atopic dermatitis, it decreased in inflammatory areas of subjects with a history of atopic dermatitis. The expressions of three markers including FABP-5, Galectin-7 and Enolase 1, shown by the Y-axis in the graphs provided in FIGS. 11A to 11C, increased more in proportion to the decrease in keratinocyte area in inflammatory areas of subjects with a history of atopic dermatitis, compared to normal areas of healthy subjects and subjects with a history of atopic dermatitis. On the other hand, the levels of expression of the remaining three markers including SCCA2, Apolipoprotein A1 and Annexin II, shown by the Y-axis in the graphs provided in FIGS. 11D to 11F, followed the order of "Healthy subjects<Normal areas of subjects with a history of atopic dermatitis<Inflammatory areas of subjects with a history of atopic dermatitis," suggesting that these markers are useful in the diagnosis of risk of developing atopic dermatitis.

INDUSTRIAL FIELD OF APPLICATION

Proteins whose expression increases or decreases according to the degree of inflammation of atopic dermatitis or risk of developing atopic dermatitis were identified. By testing the changes occurring in the expression of these proteins, more accurate diagnosis of the cause or condition of atopic dermatitis, and determination of the risk of developing atopic dermatitis, become possible. In addition, these markers can also be used, among others, in the development of treatment drugs for atopic dermatitis as well as cosmetics and health foods suitable for people with sensitive skin.

What is claimed is:

1. A method for determining atopic dermatitis, comprising measurement of the expression of a protein in skin cells and/or skin tissues, wherein the protein changes its expression with inflammation caused by atopic dermatitis, wherein the protein is Annexin II.

2. A method for determining atopic dermatitis, comprising measurement of the expression of a protein in skin cells and/or skin tissues, wherein the protein changes its expression with inflammation caused by atopic dermatitis, wherein the protein is Apolipoprotein A1.

3. The method according to claim 2, wherein the skin cells and/or skin tissues are those of the skin's horny cell layer collected using a horny cell layer checker.

4. A method for determining atopic dermatitis, comprising measurement of the expression of proteins in skin cells and/or skin tissues, wherein the proteins change their expression with inflammation caused by atopic dermatitis, wherein the proteins are Annexin II, SCCA2, and Apolipoprotein A1.

* * * * *